US012729394B2

(12) United States Patent
Dietlein et al.

(10) Patent No.: US 12,729,394 B2
(45) Date of Patent: Sep. 8, 2026

(54) IMMUNE ENHANCERS

(71) Applicant: Deutsches Krebsforschungszentrum, Heidelberg (DE)

(72) Inventors: Nikolaus Dietlein, Heidelberg (DE); Hans-Reimer Rodewald, Heidelberg (DE)

(73) Assignee: Deutsches Krebsforschungszentrum, Heidelberg (DE)

( * ) Notice: Subject to any disclaimer, the term of this patent is extended or adjusted under 35 U.S.C. 154(b) by 324 days.

(21) Appl. No.: 18/550,130

(22) PCT Filed: Mar. 10, 2022

(86) PCT No.: PCT/EP2022/056187
§ 371 (c)(1),
(2) Date: Sep. 11, 2023

(87) PCT Pub. No.: WO2022/189567
PCT Pub. Date: Sep. 15, 2022

(65) Prior Publication Data
US 2024/0150810 A1 May 9, 2024

(30) Foreign Application Priority Data
Mar. 11, 2021 (EP) .................................... 21162054

(51) Int. Cl.
*C12Q 1/34* (2006.01)

(52) U.S. Cl.
CPC .................................... *C12Q 1/34* (2013.01)

(58) Field of Classification Search
None
See application file for complete search history.

(56) References Cited

U.S. PATENT DOCUMENTS

2013/0287791 A1 10/2013 Xu et al.
2013/0344083 A1* 12/2013 Xu ...................... A61K 31/155 424/673

OTHER PUBLICATIONS

International Search Report; European Patent Office; International Application No. PCT/EP2022/056187; Jul. 12, 2022; 7 pages.
Written Opinion of the International Searching Authority; European Patent Office; International Application No. PCT/EP2022/056187; Jul. 12, 2022; 8 pages.
Wang, Yu et al.; The deubiquitinase USP22 regulates PD-L1 degradation in human cancer cells; Cell Communication and Signaling; 2020; 13 pages; vol. 18, No. 112, available at https://biosignaling.biomedcentral.com/articles/10.1186/s12964-020-00612-y.
Gao, Yayi et al.; USP22 is a positive regulator of NFATc2 on promoting IL2 expression; FEBS Letters; 2014; pp. 878-883; vol. 588.
Espinosa, Joaquín M. et al.; Histone H2B ubiquitination: the cancer connection; Genes & Development; 2008; pp. 2743-2749; vol. 22.
Jeusset, Lucile et al.; Ubiquitin Specific Peptidase 22 Regulates Histone H2B Mono-Ubiquitination and Exhibits Both Oncogenic and Tumor Suppressor Roles in Cancer; Cancers; 2017; 17 pages; vol. 9, No. 167.
Xu, Hui et al., Knock-down of ubiquitin-specific protease 22 by micro-RNA interference inhibits colorectal cancer growth, International Journal of Colorectal Disease, 2012, pp. 21-30, vol. 27.
Wang, Feng et al., Abstract 5432: Discovery and characterization of USP22 inhibitors as novel anti-cancer agents, Cancer Research, 2015, 2 pages, retrieved from the internet://cancerres.aacrjournals.org/content/75/15_Supplement/5432.
Lv, Lei et al., Silencing USP22 by asymmetric structure of interfering RNA inhibits proliferation and induces cell cycle arrest in bladder cancer cells, Molecular and Cellular Biochemistry, 2011, pp. 11-21, vol. 346.
Huang, Xing et al., Blocking PD-L1 for anti-liver cancer immunity: USP22 represents a critical cotarget, Cellular & Molecular Immunology, 2020, pp. 677-679, vol. 17.
Hong, Ahyoung et al., Ubiquitin-specific protease 22 (USP22) positively regulates RCAN1 protein levels through RCAN1 de-ubiquitination, Journal of Cellular Physiology, 2015, pp. 1651-1660, vol. 230.
Chipumuro, Edmond et al., The ubiquitin hydrolase USP22 contributes to 3'-end processing of JAK-STAT-inducible genes, The FASEB Journal, 2012, pp. 842-854, vol. 26.
Ivashkiv, Lionel B. et al., Regulation of type I interferon responses, Nature Reviews, Jan. 2014, pp. 36-49, vol. 14.
Morgan, Michael et al., Potent macrocycle inhibitors of the human SAGA deubiquitinating module, Cell Chemical Biology, 2022, pp. 544-554, vol. 29.
Roedig, Jens et al., USP22 controls necroptosis by regulating receptor-interacting protein kinase 3 ubiquitination, EMBO Reports, 2021, 21 pages, vol. 21, No. e50163.
Schneider, William M. et al., Interferon-Stimulated Genes: A Complex Web of Host Defenses, Annual Review of Immunology, 2014, pp. 513-545, vol. 32.
Zhang, Xiao-Yong et al., The Putative Cancer Stem Cell Marker USP22 Is a Subunit of the Human SAGA Complex Required for Activated Transcription and Cell-Cycle Progression, Molecular Cell, Jan. 18, 2008, pp. 102-111, vol. 29.

* cited by examiner

*Primary Examiner* — Blaine Lankford
(74) *Attorney, Agent, or Firm* — Taft Stettinius & Hollister LLP

(57) ABSTRACT

The present invention relates to an inhibitor of ubiquitin-specific peptidase 22 (Usp22 inhibitor) for use in activation of an immune response in a subject and to a kit comprising said Usp22 inhibitor. The present invention further relates to methods for identifying a subject susceptible to treatment of disease by administration of a Usp22 inhibitor and for identifying a compound for activation of an immune response in a subject, as well as to a medicament for treating and/or preventing cancer or an infection comprising (i) a Usp22 inhibitor and (ii) a pharmaceutically acceptable carrier.

10 Claims, 9 Drawing Sheets

Figure 1:
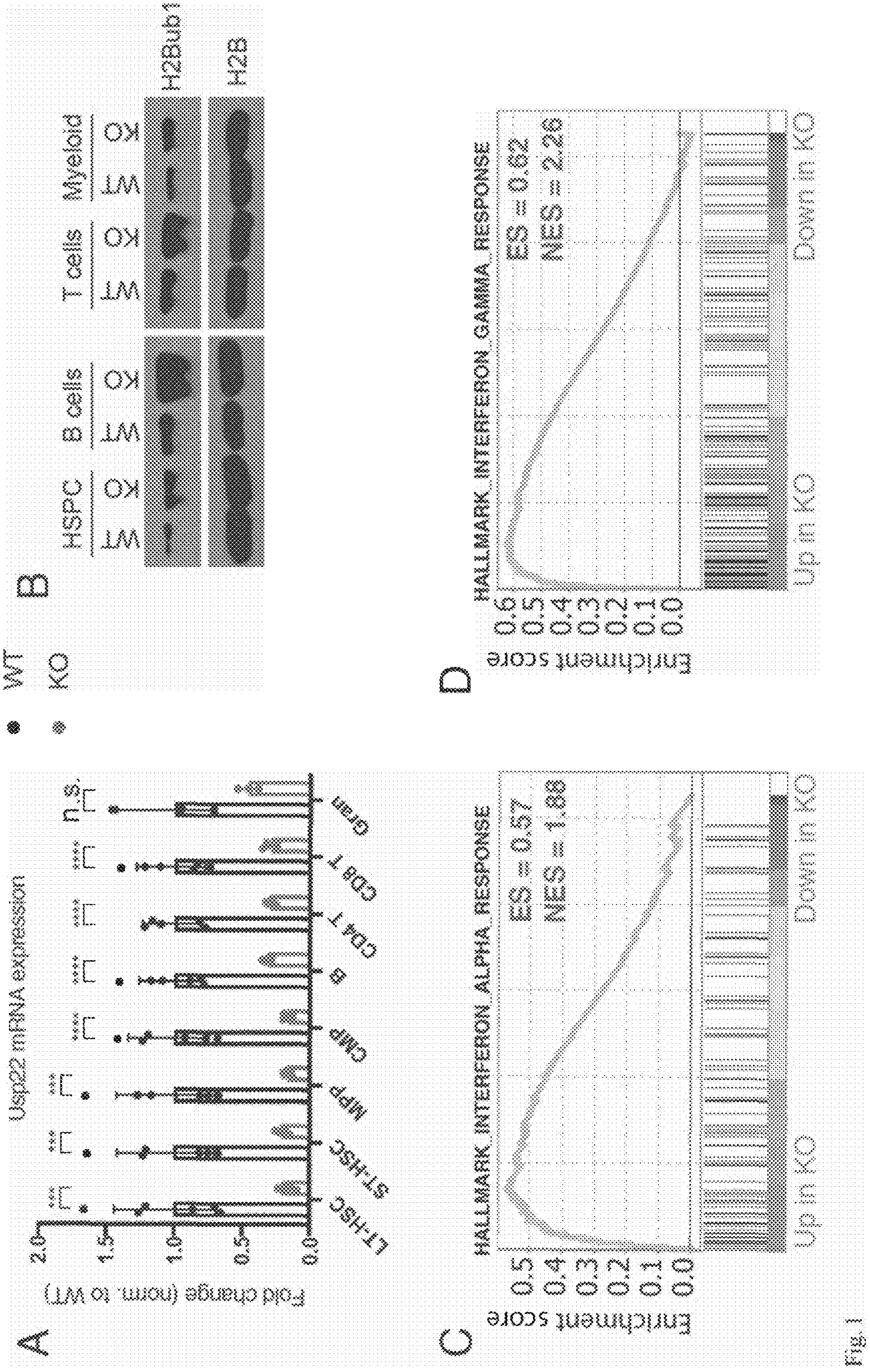
Figure 1:
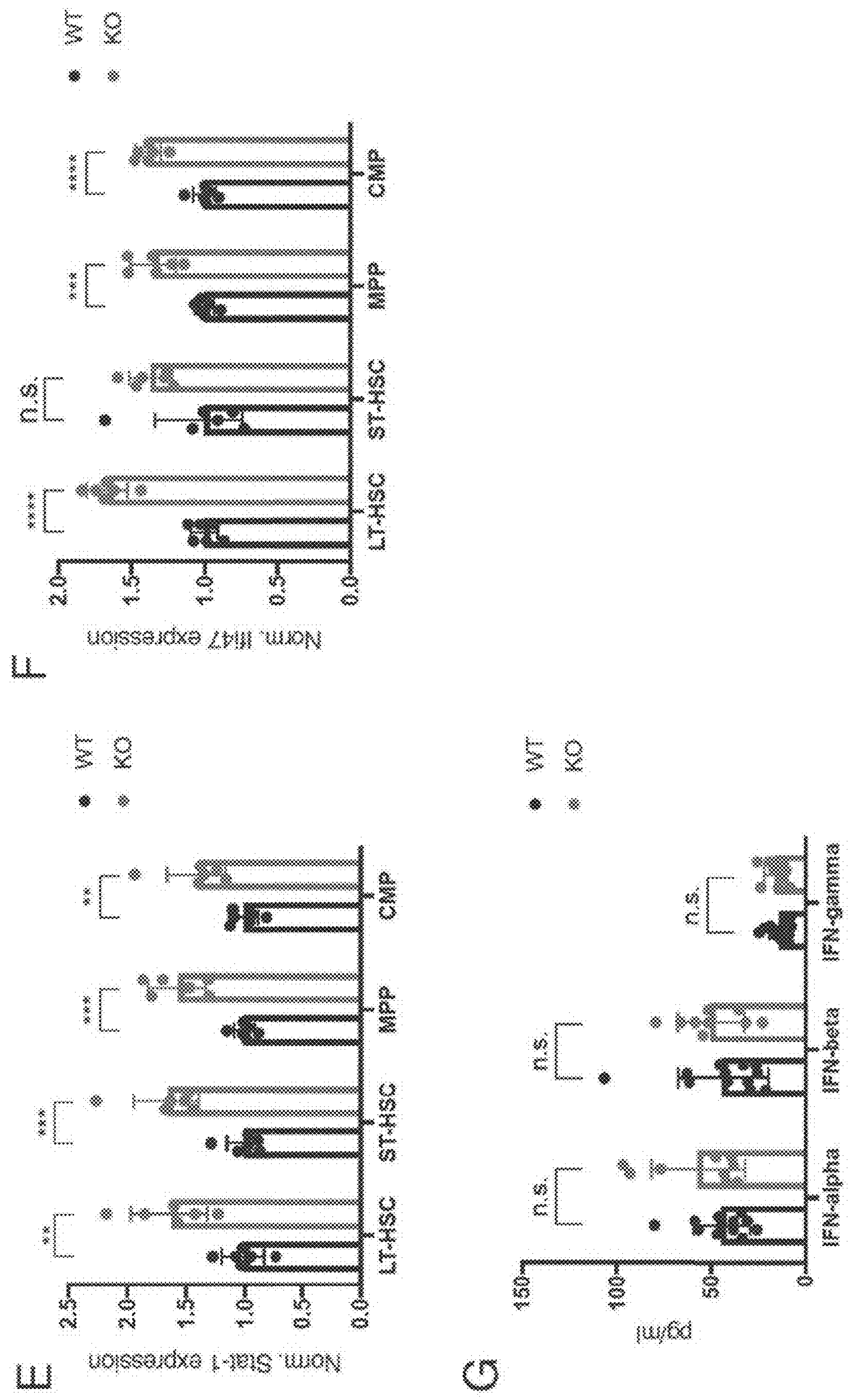

Specification includes a Sequence Listing.

E

A
WT
KO
CD44 BV605
7.7 %
80.1 %
15.2 %
67.3 %
B
% of CD4+
100
80
60
40
20
10
0
****
**
Naive
Activated
WT
KO
C
WT
KO
0.7 %
2.5 %
PD-1 AF647
CXCR5 PE
D
$T_{FH}$ cells
**
% of CD4+
5
4
3
2
1
0
WT
KO Fluorescence (A.U.)

6×10^6

4×10^6

2×10^6

0

0 10 20 30 40 50 60

Time (min)

No enzyme

USP22 w/o BSA

USP22 + BSA

IMMUNE ENHANCERS

CROSS-REFERENCE TO RELATED APPLICATIONS

This application is a U.S. National Phase of International PCT Application No. PCT/EP2022/056187 filed on Mar. 10, 2022, which claims priority to European Patent Application No. 21162054.7 filed on Mar. 11, 2021, the contents of each application are incorporated herein by reference in their entirety.

The present invention relates to an inhibitor of ubiquitin-specific peptidase 22(Usp22 inhibitor) for use in activation of an immune response in a subject and to a kit comprising said Usp22 inhibitor. The present invention further relates to methods for identifying a subject susceptible to treatment of disease by administration of a Usp22 inhibitor and for identifying a compound for activation of an immune response in a subject, as well as to a medicament for treating and/or preventing cancer or an infection comprising (i) a Usp22 inhibitor and (ii) a pharmaceutically acceptable carrier.

Interferons are cytokines produced upon viral and bacterial infections which exert their function through the induction of several hundred interferon-stimulated genes (ISGs). On the cellular level, 1SG expression confers an anti-viral state by a plethora of mechanisms, including inhibition of viral entry and replication (reviewed by Schneider et al., Annu. Rev. Immunol. 32, 513-545 (2014)). Organismal interferon-mediated effects include HSC activation, increased myelopoiesis, impaired B-cell development, spontaneous T cell activation as well as increased germinal center formation, enhanced plasma cell differentiation and increased immunoglobulin production (reviewed in Ivashkiv et al, Nature Rev Immunol 14, 36-49 (2014)). It is unclear whether there is a unifying chromatin state underlying such diverse responses across the immune system.

Monoubiquitinated H2B (H2Bub1) is an activating chromatin mark found in the transcribed regions of highly expressed genes. In mammalian cells, H2B monoubiquitination is catalyzed by the Rnf20/Rnf40 E3 ubiquitin ligase complex. Usp22 is the enzymatically active component of the SAGA DUB module and acts as an H2Bub1 deubiquitinase (Zhang et al, Molecular Cell 29, 102-111 (2008)). Usp22 was found to be involved in a variety of cancer-related pathways (reviewed in Jeusset & MacManus, Cancers 9:167 (2017)), including necroptosis (Roedig et al. (2020), EMBO reports 22:e50163), and screenings for Usp22 inhibitors were reported (Wang et al., Cancer Res 75(15) Supplement:Abstract 5432), with results not publicly available, and Morgan et al. (2021), Cell Chem Biol 29:1-11 (doi.ogg/10.1016/j.chembiol.2021.12.004), identifying inhibitory cyclic peptides).

There is, nonetheless, a need in the art for improved means and methods for activation of an immune response in a subject. This problem is solved by the subject matter of the instant invention.

In accordance, the present invention relates to an inhibitor of Ubiquitin-specific peptidase 22 (Usp22 inhibitor) for use in activation of an immune response in a subject.

In general, terms used herein are to be given their ordinary and customary meaning to a person of ordinary skill in the art and, unless indicated otherwise, are not to be limited to a special or customized meaning. As used in the following, the terms "have", "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B", "A comprises B" and "A includes B" may both refer to a situation in which, besides B, no other element is present in A (i.e. a situation in which A solely and exclusively consists of B) and to a situation in which, besides B, one or more further elements are present in entity A, such as element C, elements C and D or even further elements. Also, as is understood by the skilled person, the expressions "comprising a" and "comprising an" preferably refer to "comprising one or more", i.e. are equivalent to "comprising at least one".

Further, as used in the following, the terms "preferably", "more preferably", "most preferably", "particularly", "more particularly", "specifically", "more specifically" or similar terms are used in conjunction with optional features, without restricting further possibilities. Thus, features introduced by these terms are optional features and are not intended to restrict the scope of the claims in any way. The invention may, as the skilled person will recognize, be performed by using alternative features. Similarly, features introduced by "in an embodiment" or similar expressions are intended to be optional features, without any restriction regarding further embodiments of the invention, without any restrictions regarding the scope of the invention and without any restriction regarding the possibility of combining the features introduced in such way with other optional or non-optional features of the invention.

The methods specified herein below, preferably, are in vitro methods. The method steps may, in principle, be performed in any arbitrary sequence deemed suitable by the skilled person, but preferably are performed in the indicated sequence; also, one or more, preferably all, of said steps may be assisted or performed by automated equipment. Moreover, the methods may comprise steps in addition to those explicitly mentioned above.

As used herein, the term "standard conditions", if not otherwise noted, relates to IUPAC standard ambient temperature and pressure (SATP) conditions, i.e. preferably, a temperature of 25° C. and an absolute pressure of 100 kPa; also preferably, standard conditions include a pH of 7. Moreover, if not otherwise indicated, the term "about" relates to the indicated value with the commonly accepted technical precision in the relevant field, preferably relates to the indicated value ±20%, more preferably ±10%, most preferably ±5%. Further, the term "essentially" indicates that deviations having influence on the indicated result or use are absent, i.e. potential deviations do not cause the indicated result to deviate by more than ±20%, more preferably±10%, most preferably ±5%. Thus, "consisting essentially of" means including the components specified but excluding other components except for materials present as impurities, unavoidable materials present as a result of processes used to provide the components, and components added for a purpose other than achieving the technical effect of the invention. For example, a composition defined using the phrase "consisting essentially of" encompasses any known acceptable additive, excipient, diluent, carrier, and the like. Preferably, a composition consisting essentially of a set of components will comprise less than 5% by weight, more preferably less than 3% by weight, even more preferably less than 1% by weight, most preferably less than 0.1% by weight of non-specified component(s).

The degree of identity (e.g. expressed as "% identity") between two biological sequences, preferably DNA, RNA, or amino acid sequences, can be determined by algorithms well known in the art. Preferably, the degree of identity is determined by comparing two optimally aligned sequences over a comparison window, where the fragment of sequence in the comparison window may comprise additions or deletions (e.g., gaps or overhangs) as compared to the sequence it is compared to for optimal alignment. The percentage is calculated by determining, preferably over the whole length of the polynucleotide or polypeptide, the number of positions at which the identical residue occurs in both sequences to yield the number of matched positions, dividing the number of matched positions by the total number of positions in the window of comparison and multiplying the result by 100 to yield the percentage of sequence identity. Optimal alignment of sequences for comparison may be conducted by the local homology algorithm of Smith and Waterman (1981), by the homology alignment algorithm of Needleman and Wunsch (1970), by the search for similarity method of Pearson and Lipman (1988), by computerized implementations of these algorithms (GAP, BESTFIT, BLAST, PASTA, and TFASTA in the Wisconsin Genetics Software Package, Genetics Computer Group (GCG), 575 Science Dr., Madison, WI), or by visual inspection. Given that two sequences have been identified for comparison, GAP and BESTFIT are preferably employed to determine their optimal alignment and, thus, the degree of identity. Preferably, the default values of 5.00 for gap weight and 0.30 for gap weight length are used. In the context of biological sequences referred to herein, the term "essentially identical" indicates a % identity value of at least 80%, preferably at least 90%/, more preferably at least 98%, most preferably at least 99%. As will be understood, the term essentially identical includes 100% identity. The aforesaid applies to the term "essentially complementary" mutatis mutandis.

Unless specifically indicated otherwise herein, the compounds specified, in particular the polynucleotides and polypeptides, may be comprised in larger structures, e.g. may be covalently or non-covalently linked to further sequences, carrier molecules, retardants, and other excipients. In particular, polypeptides as specified may be comprised in fusion polypeptides comprising further peptides, which may serve e.g. as a tag for purification and/or detection, as a linker, or to extend the in vivo half-life of a compound. The term "detectable tag" refers to a stretch of amino acids which are added to or introduced into the fusion polypeptide; preferably, the tag is added C- or N-terminally to the fusion polypeptide. Said stretch of amino acids preferably allows for detection of the polypeptide by an antibody which specifically recognizes the tag; or it preferably allows for forming a functional conformation, such as a chelator; or it preferably allows for visualization, e.g. in the case of fluorescent tags. Preferred detectable tags are the Myc-tag, FLAG-tag, 6-His-tag, HA-tag, GST-tag or a fluorescent protein tag, e.g. a GFP-tag. These tags are all well known in the art. Other further peptides preferably comprised in a fusion polypeptide comprise further amino acids or other modifications which may serve as mediators of secretion, as mediators of blood-brain-barrier passage, as cell-penetrating peptides, and/or as immune stimulants. Further polypeptides or peptides to which the polypeptides may be fused are signal and/or transport sequences, e.g. an IL-2 signal sequence, and linker sequences, The term "polypeptide", as used herein, refers to a molecule consisting of several, typically at least 20 amino acids that are covalently linked to each other by peptide bonds. Molecules consisting of less than 20 amino acids covalently linked by peptide bonds are usually considered to be "peptides". Preferably, the polypeptide comprises of from 50 to 1000, more preferably of from 75 to 1000, still more preferably of from 100 to 500, most preferably of from 110 to 400 amino acids. Preferably, the polypeptide is comprised in a fusion polypeptide and/or a polypeptide complex.

The term "ubiquitin" is known to the skilled person to relate to a group of small polypeptides ubiquitous in mammalian organisms and having functions in modulating degradation, cellular location, activity, and interactions of proteins. Database entries for human ubiquitin can be found e.g. in Genbank Acc No: CAA44911.1 and in UniProtKB entry P62979 (v2 of Aug. 10, 2010). The terms "histone" and "histone 2B", the latter abbreviated as "BM", are known to the skilled person as well. Database entries for human H2B can be found e.g. in Genbank Acc No: NP_003519.1. The mono-ubiquitinylated form of H2B is referred to herein as H2Bub1.

The term "ubiquitin-specific peptidase", abbreviated as "Usp", as used herein, relates to a member of a family of enzymes removing ubiquitin-conjugates from cellular proteins and which are therefore also referred to as "deubiquitinating enzymes" or as "deubiquitinases", E.C. 3.4.19.12. In accordance, the term "ubiquitin-specific peptidase 22", abbreviated as "Usp22", relates to the human deubiquitinase known under this designation and to any variant thereof as specified herein below, having the biological activity of removing ubiquitin from ubiquitin-conjugated histone 2B (H2Bub1). Thus, preferably, Usp22 is a polypeptide comprising the amino acid sequence of Genbank Acc NO.: XP_005256632.1, or is a variant thereof. More preferably Usp22 is a polypeptide comprising the amino acid sequence of Genbank Acc NO.: XP_005256632.1 or is a homolog or isoform thereof. Most preferably, Usp22 is a polypeptide comprising the amino acid of Genbank Acc NO.: XP_005256632.1 or an isoform thereof. Isoforms of Usp22 are e.g. shown in UniProtKB entry Q9UPT9 as of Oct. 7, 2020.

The terms "inhibitor of ubiquitin-specific peptidase 22" and "Usp22 inhibitor" relate to a compound significantly reducing, preferably abolishing, activity of Usp22 in a target cell, wherein "significantly reducing activity" preferably relates to a reduction of measurable activity by at least 50%, more preferably by at least 75%, most preferably by at least 90%. Preferably, the Usp22 inhibitor is an unspecific Usp inhibitor, i.e. is an inhibitor inhibiting several Usps including Usp22. More preferably, the Usp22 inhibitor is a specific Usp22 inhibitor, i.e. is an inhibitor inhibiting only Usp22 activity, still more preferably inhibits only removal of ubiquitin from H2Bub1. Preferably, the specific Usp22 inhibitor inhibits Usp activity other than Usp22 activity only by at most 50%, preferably at most 25%, more preferably by at most 10% at a concentration inhibiting Usp22 activity by 90%. The activity of an inhibitor of Usp22 is, preferably, determined in vitro by assaying the enzymatic activity of Usp22 as specified elsewhere herein. Also preferably, the activity of an inhibitor of Usp22 is determined in vivo or in cultured host cells by determining the intracellular H2Bub1 concentration in a host cell contacted with a putative or known inhibitor of Usp22. As shown elsewhere herein, if a host cell is contacted with an inhibitor of Usp22, the intracellular concentration of H2Bub1 increases compared to a value measurable in a control host cell. Also preferably, the activity of an inhibitor of Usp22 is determined in vivo by determining myeloid bias in white blood cells, preferably as shown herein in the Examples.

Preferably, the Usp22 inhibitor is a direct Usp22 inhibitor, i.e., preferably, is a compound directly interacting with Usp22 and, thereby, inhibiting Usp22 activity. Preferably, the direct inhibitor of Usp22 is a polypeptide or polynucleotide specifically binding Usp22 and inhibiting Usp22. More preferably, the direct inhibitor of Usp22 is a polypeptide specifically binding and inhibiting Usp22, i.e. is an inhibitory polypeptide. More preferably, the direct inhibitor of Usp22 is a polypeptide specifically binding and inhibiting Usp22 selected from the list consisting of an antibody, a peptide aptamer, an anticalin, and a Designed Ankyrin Repeat Protein (DARPin), most preferably is an antibody. Also more preferably, the direct inhibitor of Usp22 is a polynucleotide specifically binding and inhibiting Usp22, preferably a polynucleotide aptamer. Preferably, the direct inhibitor of Usp22 is a compound binding to at least one epitope in Usp22, preferably an epitope including at least one amino acid of the active center of Usp22. The skilled person is aware of methods suitable for determining binding of a direct inhibitor to Usp22, e.g. staining of Usp22-positive cells or of extracts from such cells with a direct inhibitor, wherein said inhibitor is coupled to a detectable label, preferably a colored and/or fluorescent dye; ELISA methods; surface plasmon resonance methods, and the like.

In a preferred embodiment, the USP22 inhibitor is an inhibitory peptide. Thus, the USP22 inhibitor in a preferred embodiment is a peptide comprising, more preferably consisting of, an amino acid sequence selected from the group consisting of SEQ ID NOs:1 to 8, more preferably SEQ ID NO:1; wherein the N-terminal amino acid in SEQ ID NO:1, 3, 4, 5, 6, and 8 preferably is a D-amino acid. In a more preferred embodiment, the USP22 inhibitor is a cyclic peptide comprising, more preferably consisting of, an amino acid sequence selected from the group consisting of SEQ ID NOs:9 to 17, more preferably SEQ ID NO:9; wherein the N-terminal amino acid in SEQ ID NO:9, 12,13, 14, 15, and 17 preferably is a D-amino acid, and wherein the C-terminal cysteine formed a thioether with an upstream N-chloroacetyl-amino acid, preferably in position 1 of the respective peptide. Thus, in a preferred embodiment, the USP22 inhibitor is a cyclic inhibitory peptide as known from Morgan et al. (2021), Cell Chem Biol 29:1-11 (doi.org/10.1016/j.chembiol.2021.12.004).

As used herein, the term "antibody" relates to a soluble immunoglobulin from any of the classes IgA, IgD, IgE, IgG, or IgM, having the activity of directly interacting with Usp22 and inhibiting Usp22 activity as specified herein above. Antibodies against Usp22 can be prepared by well-known methods using a purified Usp22 polypeptide or a suitable fragment derived therefrom as an antigen. A fragment which is suitable as an antigen may be identified by antigenicity determining algorithms well known in the art. Suitable fragments may also be obtained either from the Usp22 polypeptide by proteolytic digestion, may be synthetic peptides, or may be recombinantly expressed. Suitability of an antibody thus generated as an inhibitor of Usp22 can be tested by an assay as described elsewhere herein. Preferably, the antibody of the present invention is a monoclonal antibody, a human, primatized, chimerized, or humanized antibody, or a fragment thereof. More preferably, the antibody is a single chain antibody, a single-domain antibody, a nanobody, or an antibody fragment, such as Fab, scFab, and the like. Also comprised as antibodies of the present invention are a bispecific antibody, a synthetic antibody, or a chemically modified derivative of any of the aforesaid antibodies. Preferably, the antibody of the present invention shall specifically bind (i.e. does not cross react with other polypeptides or peptides) to a Usp22 polypeptide as specified above. Specific binding can be tested by various well-known techniques. Antibodies or fragments thereof can be obtained by using methods described, e.g., in Harlow and Lane "Antibodies, A Laboratory Manual", CSH Press, Cold Spring Harbor, 1988. Monoclonal antibodies can be prepared by the techniques originally described in Köhler and Milstein, Nature. 1975. 256: 495; and Galfrd, Meth. Enzymol. 1981, 73: 3, which comprise the fusion of mouse myeloma cells to spleen cells derived from immunized mammals. Preferably, the antibody is an antibody as specified above or a polypeptide derivative thereof, more preferably, the antibody is an antibody as specified above.

As used herein, the term "aptamer" relates to a polynucleotide or polypeptide binding specifically to a target molecule by virtue of its three-dimensional structure. Preferably, the aptamer is a peptide aptamer, a "peptide aptamer" preferably being a peptide specifically interacting with Usp22 and, thereby, inhibiting Usp22 activity as specified herein above. Peptide aptamers, preferably, are peptides comprising 8-80 amino acids, more preferably 10-50 amino acids, and most preferably 15-30 amino acids. They can e.g. be isolated from randomized peptide expression libraries in a suitable host system like baker's yeast (see, for example, Klevenz et al, Cell Mol Life Sci. 2002, 59: 1993-1998). A peptide aptamer, preferably, is a free peptide; it is, however, also contemplated that a peptide aptamer is fused to a polypeptide serving as "scaffold", meaning that the covalent linking to said polypeptide serves to fix the three-dimensional structure of said peptide aptamer to a specific conformation. More preferably, the peptide aptamer is fused to a transport signal, in particular a cell-penetrating peptide. Preferably, the aptamer is an aptamer as specified above or a polypeptide or polynucleotide derivative thereof, more preferably, the aptamer is an aptamer as specified above.

As used herein, the term "anticalin" relates to an artificial polypeptide derived from a lipocalin specifically binding Usp22 and inhibiting Usp22 activity. Similarly, a "Designed Ankyrin Repeat Protein" or "DARPin", as used herein, is an artificial polypeptide, comprising several ankyrin repeat motifs, specifically binding Usp22 and inhibiting Usp22 activity. Preferably, the anticalin or DARPin is an anticalin or DARPin as specified above or a polypeptide derivative thereof; more preferably, the anticalin or DARPin is an anticalin or DARPin as specified above.

Also preferably, the Usp22 inhibitor is an indirect Usp22 inhibitor, i.e. a compound not directly inhibiting Usp22 activity, but still significantly reducing, preferably preventing, Usp22 activity in a target cell. Preferably, the indirect Usp22 inhibitor specifically binds to a Usp22 encoding polynucleotide, preferably thereby significantly reducing, more preferably preventing, Usp22 expression. Also preferably, the indirect Usp22 inhibitor is or binds, preferably specifically binds, to a transcriptional regulator of the Usp22 gene, preferably thereby significantly reducing, more preferably preventing, Usp22 transcription. Thus, the indirect Usp22 inhibitor may be a transcriptional repressor of Usp22 transcription, e.g. Sp1 or may be an inhibitor of a transcriptional activator of Usp22 transcription, e.g. H-89.

Preferably, the indirect Usp22 inhibitor is a polynucleotide, preferably a polynucleotide inhibiting expression or inducing degradation of a Usp22 mRNA. More preferably, the indirect Usp22 inhibitor is selected from the group consisting of an shRNA, an siRNA, a ribozyme, an antisense molecule, an inhibitory oligonucleotide, and a micro RNA. Most preferably, the indirect Usp22 inhibitor is an shRNA.

It is understood by the skilled person that inhibition of expression or induction of degradation of a specific RNA can be achieved in various ways. It is also understood by the skilled person that the exact embodiment of a polynucleotide being an indirect Usp22 inhibitor of the present invention will depend on the treatment intended.

Preferably, the indirect Usp22 inhibitor is a ribozyme. The term "ribozyme" as used herein refers to catalytic RNA molecules possessing a well-defined tertiary structure that allows for catalyzing either the hydrolysis of one of their own phosphodiester bonds (self-cleaving ribozymes), or the hydrolysis of bonds in other RNAs, but they have also been found to catalyze the aminotransferase activity of the ribosome. The ribozymes envisaged in accordance with the present invention are, preferably, those which specifically hydrolyze the target RNAs, preferably Usp22 mRNA, i.e., preferably RNA transcribed from a Usp22 gene. In particular, hammerhead ribozymes are preferred in accordance with the present invention. How to generate and use such ribozymes is well known in the art (see, e.g., Hean & Weinberg (2008), RNA and the Regulation of Gene Expression: A Hidden Layer of Complexity, Chapter 1. Caister Academic Press).

Also preferably, the indirect Usp22 inhibitor is a polypeptide comprising a lysosome-degradation sequence, preferably a chaperone-mediated autophagy-targeting motif (CTM). Preferably, said CTM-comprising polypeptide specifically binds to Usp22; e.g. the CTM-comprising polypeptide may further comprise an antibody specifically binding to Usp22. As the skilled person will understand, the CTM-conjugated antibody does not necessarily have to be an inhibitory Usp22 antibody as specified herein above; it is, however, preferred that the antibody is a Usp-specific antibody, more preferably a Usp22-specific antibody. Preferably, the CTM-comprising polypeptide specifically binding to Usp22 binds to Usp22 with a $K_D$ value at least 10fold, preferably at least 20fold, more preferably at least 50fold, most preferably at least 100fold higher than the $K_D$ value of said CTM-comprising polypeptide for other Usps. More preferably, the CTM-comprising polypeptide specifically binding to Usp22 does not detectably bind to other cellular proteins, preferably including non-Usp22 Usps. As will be understood by the skilled person, in case the indirect Usp22 inhibitor is a CTM-comprising polypeptide, said CTM-comprising polypeptide does not have to be, but may be, a direct inhibitor of Usp22. Thus, preferably, the CTM-comprising polypeptide also is a direct inhibitor of Usp22.

More preferably, the indirect Usp22 inhibitor is an antisense oligonucleotide. The term "antisense oligonucleotide" is known to the skilled person and relates to an oligonucleotide hybridizing to a target RNA, causing the formation of a DNA/RNA hybrid. Said DNA/RNA hybrid is a substrate for RNase H, which degrades the RNA portion of said DNA/RNA hybrid. Thus, the antisense oligonucleotide comprises at least five, preferably at least seven, more preferably at least nine, or, most preferably, at least ten DNA nucleotides. Preferably, the antisense oligonucleotide has a length of at least 15 nucleotides, preferably at least 18 nucleotides, still more preferably at least 20 nucleotides.

Most preferably, the indirect Usp22 inhibitor is a polynucleotide inducing RNA interference. As used herein, "RNA interference (RNAi)" refers to sequence-specific, post-transcriptional gene silencing of a selected target gene by degradation of RNA transcribed from the target gene (target RNA). Target RNAs, preferably, are Usp22 mRNAs, i.e. RNAs transcribed from a Usp22 gene as specified above. It is to be understood that silencing as used herein does not necessarily mean the complete abolishment of expression. RNAi, preferably, reduces expression by at least 40%, more preferably at least 60%, even more preferably at least 80%, most preferably at least 90/6 as compared to the expression level in a reference without RNAi. RNAi requires in the target cell the presence of dsRNAs that are homologous in sequence to the target RNAs. The term "dsRNA" refers to RNA having a duplex structure comprising two complementary and anti-parallel nucleic acid strands. The RNA strands forming the dsRNA may have the same or a different number of nucleotides, whereby one of the strands of the dsRNA can be the target RNA. It is, however, also contemplated by the present invention that the dsRNA is formed between two sequence stretches on the same RNA molecule, e.g. by formation of a stem-loop structure. RNAi may be used to specifically inhibit expression of the target RNAs of the present invention in vivo. Accordingly, it may be used for the medical uses as specified elsewhere herein. For such therapeutic approaches, expression constructs for siRNA may be introduced into target cells of the host. Accordingly, siRNA may be combined efficiently with other therapy approaches. Methods relating to the use of RNAi to silence genes in animals, including mammals, are known in the art.

Thus, the indirect inhibitor of Usp22, preferably is an RNAi agent. As used herein, the term "RNAi agent" refers to an shRNA, a siRNA agent, or a miRNA agent as specified below. The RNAi agent of the present invention is of sufficient length and complementarity to stably interact with the target RNA, i.e. it comprises at least 15, at least 17, at least 19, at least 21, at least 22 nucleotides complementary to the target RNA. By "stably interact" is meant interaction of the RNAi agent or its products produced by the target cell with a target RNA, e.g., by forming hydrogen bonds with complementary nucleotides in the target RNA under physiological conditions.

The term "siRNA agent" as meant herein encompasses: a) a dSRNA consisting of at least 15, at least 17, at least 19, at least 21 consecutive nucleotides base-paired, i.e. forming hydrogen bonds with complementary nucleotides. b) a small interfering RNA (siRNA) molecule or a molecule comprising an siRNA molecule. The siRNA is a single-stranded RNA molecule with a length, preferably, greater than or equal to 15 nucleotides and, preferably, a length of 15 to 49 nucleotides, more preferably 17 to 30 nucleotides, and most preferably 17 to 30 nucleotides, preferably 17, 18, 19, 20, 21, 22, 23, 24, 25, 26, 27, 28, 29, or 30 nucleotides. According to the present invention, the term "molecule comprising an siRNA molecule" includes RNA molecules from which an siRNA is processed by a cell, preferably by a mammalian cell. Thus, a molecule comprising an siRNA molecule, preferably, is a small hairpin RNA, also known as shRNA. As used herein, the term "shRNA" relates to a, preferably artificial, RNA molecule forming a stem-loop structure comprising at least 10, preferably at least 15, more preferably at least 17, most preferably at least 20 nucleotides base-paired to a complementary sequence on the same mRNA molecule ("stem"), i.e. as a dsRNA, separated by a stretch of non-base-paired nucleotides ("loop"). c) a polynucleotide encoding a) or b), wherein, preferably, said polynucleotide is operatively linked to an expression control sequence. Thus, the function of the siRNA agent to inhibit expression of the target gene can be modulated by said expression control sequence. Preferred expression control sequences are those, which can be regulated by exogenous stimuli, e.g. the tet operator, whose activity can be regulated by tetracycline, or heat inducible promoters. Alternatively or in addition, one or more expression control sequences can be used which allow tissue-specific expression of the siRNA agent.

It is, however, also contemplated by the current invention that the RNAi agent is a miRNA agent. A "miRNA agent" as meant herein encompasses: a) a pre-microRNA, i.e. an mRNA comprising at least 30, at least 40, at least 50, at least 60, at least 70 nucleotides base-paired to a complementary sequence on the same mRNA molecule ("stem"), i.e. as a dsRNA, separated by a stretch of non-base-paired nucleotides ("loop"). b) a pre-microRNA, i.e. a dsRNA molecule comprising a stretch of at least 19, at least 20, at least 21, at least 22, at least 23, at least 24, at least 25 base-paired nucleotides formed by nucleotides of the same RNA molecule (stem), separated by a loop. c) a microRNA (miRNA), i.e. a dsRNA comprising at least 15, at least 17, at least 18, at least 19, at least 21 nucleotides on two separate RNA strands. d) a polynucleotide encoding a) or b), wherein, preferably, said polynucleotide is operatively linked to an expression control sequence as specified above.

Also preferably, the indirect inhibitor of Usp22 comprises two CRISPR/Cas oligonucleotides. The CRISPR/Cas system has been known for several years as a convenient system for inducing knock-out mutations, i.e. deletions, preferably of chromosomal genes. The skilled person knows how to design appropriate oligonucleotides, which are, preferably, expressed from a vector, to induce deletion of a DNA sequence of interest. Preferably, said deletion is a partial deletion, more preferably deletion of a portion of the gene essential for function; most preferably said deletion is a complete deletion of at least the whole coding region.

As used herein, the term "polypeptide variant" relates to any chemical molecule comprising at least one polypeptide as specified above, having the indicated activity, but differing in structure from said polypeptide indicated above. Preferably, the polypeptide variant comprises a peptide having an amino acid sequence corresponding to an amino acid sequence of 5 to 200, more preferably 6 to 100, even more preferably 7 to 50, or, most preferably, 8 to 30 consecutive amino acids comprised in a polypeptide as specified above. Moreover, also encompassed are further polypeptide variants of the aforementioned polypeptides. Such polypeptide variants have at least the same essential biological activity as the specific polypeptides. Moreover, it is to be understood that a polypeptide variant as referred to in accordance with the present invention shall have an amino acid sequence which differs due to at least one amino acid substitution, deletion and/or addition, wherein the amino acid sequence of the variant is still, preferably, at least 50%, 60%, 70%, 80%, 85%, 90%, 92%, 95%, 97%, 98%, or 99% identical with the amino acid sequence of the specific polypeptide. The degree of identity between two amino acid sequences can be determined by algorithms well known in the art. Preferably, the degree of identity is to be determined by comparing two optimally aligned sequences over a comparison window, where the fragment of amino acid sequence in the comparison window may comprise additions or deletions (e.g., gaps or overhangs) as compared to the sequence it is compared to for optimal alignment. The percentage is calculated by determining, preferably over the whole length of the peptide, the number of positions at which the identical amino acid residue occurs in both sequences to yield the number of matched positions, dividing the number of matched positions by the total number of positions in the window of comparison and multiplying the result by 100 to yield the percentage of sequence identity. Optimal alignment of sequences for comparison may be conducted by the local homology algorithm of Smith and Waterman (1981), by the homology alignment algorithm of Needleman and Wunsch (1970), by the search for similarity method of Pearson and Lipman (1988), by computerized implementations of these algorithms (GAP, BESTFIT, BLAST, PASTA, and TFASTA in the Wisconsin Genetics Software Package, Genetics Computer Group (GCG), 575 Science Dr., Madison, WI), or by visual inspection. Given that two sequences have been identified for comparison, GAP and BESTFIT are preferably employed to determine their optimal alignment and, thus, the degree of identity. Preferably, the default values of 5.00 for gap weight and 0.30 for gap weight length are used. Polypeptide variants referred to above may be allelic variants or any other species specific homologs, paralogs, or orthologs. Moreover, the polypeptide variants referred to herein include fragments of the specific polypeptides or the aforementioned types of polypeptide variants as long as these fragments and/or variants have the biological activity as referred to above. Such fragments may be or may be derived from, e.g., degradation products or splice variants of the polypeptides. Further included are variants, which differ due to posttranslational modifications such as phosphorylation, glycosylation, ubiquitinylation, sumoylation, or myristylation, by including non-natural amino acids, and/or by being peptidomimetics.

The term "polynucleotide variant", as used herein, relates to a variant of a polynucleotide related to herein comprising a nucleic acid sequence characterized in that the sequence can be derived for the aforementioned specific nucleic acid sequence by at least one nucleotide substitution, addition and/or deletion, wherein the polynucleotide variant shall have the activity as specified for the specific polynucleotide. Moreover, it is to be understood that a polynucleotide variant as referred to in accordance with the present invention shall have a nucleic acid sequence, which differs due to at least one nucleotide substitution, deletion and/or addition. Preferably, said polynucleotide variant is an ortholog, a paralog or another homolog of the specific polynucleotide. Also preferably, said polynucleotide variant is a non-naturally occurring allele of the specific polynucleotide. Polynucleotide variants also encompass polynucleotides comprising a nucleic acid sequence, which is capable of hybridizing to the aforementioned specific polynucleotides, preferably, under stringent hybridization conditions. These stringent conditions are known to the skilled worker and can be found in Current Protocols in Molecular Biology, John Wiley & Sons, N. Y. (1989), 6.3.1-6.3.6. A preferred example for stringent hybridization conditions are hybridization conditions in 6x sodium chloride/sodium citrate (=SSC) at approximately 45° C., followed by one or more wash steps in 0.2×SSC, 0.1% SDS at 50 to 65° C. The skilled worker knows that these hybridization conditions differ depending on the type of nucleic acid and, for example when organic solvents are present, with regard to the temperature and concentration of the buffer. For example, under "standard hybridization conditions" the temperature differs depending on the type of nucleic acid between 42° C. and 58° C. in aqueous buffer with a concentration of 0.1× to 5×SSC (pH 7.2). If organic solvent is present in the abovementioned buffer, for example 50% formamide, the temperature under standard conditions is approximately 42° C. The hybridization conditions for DNA-DNA hybrids are preferably for example 0.1×SSC and 20° C. to 45° C., preferably between 30° C. and 45° C. The hybridization conditions for DNA:RNA hybrids are preferably, for example, 0.1×SSC and 30° C. to 55° C., preferably between 45° C. and 55° C. The abovementioned hybridization temperatures are determined for example for a nucleic acid with approximately 100 bp (=base pairs) in length and a G+C content of 50% in the absence of formamide. The skilled worker knows how to determine the hybridization conditions required by referring to textbooks such as the textbook mentioned above, or the following textbooks: Sambrook et al., "Molecular Cloning", Cold Spring Harbor Laboratory, 1989; Hames and Higgins (Ed.) 1985, "Nucleic Acids Hybridization: A Practical Approach", IRL Press at Oxford University Press, Oxford; Brown (Ed.) 1991, "Essential Molecular Biology: A Practical Approach", IRL Press at Oxford University Press, Oxford. Alternatively, polynucleotide variants are obtainable by PCR-based techniques such as mixed oligonucleotide primer-based amplification of DNA, i.e. using degenerated primers against conserved domains of a polypeptide of the present invention. Conserved domains of a polypeptide may be identified by a sequence comparison of the nucleic acid sequence of the polynucleotide or the amino acid sequence of the polypeptide of the present invention with sequences of other organisms. As a template, DNA or cDNA from bacteria, fungi, plants or, preferably, from animals may be used. Further, variants include polynucleotides comprising nucleic acid sequences which are at least 70%, at least 75%, at least 80%, at least 85%, at least 90%, at least 95%, at least 98% or at least 99% identical to the specifically indicated nucleic acid sequences. Moreover, also encompassed are polynucleotides which comprise nucleic acid sequences encoding amino acid sequences which are at least 70%, at least 75%, at least 80%, at least 85%, at least 90%, at least 95%, at least 98% or at least 99% identical to the amino acid sequences specifically indicated. The percent identity values are, preferably, calculated over the entire amino acid or nucleic acid sequence region. A series of programs based on a variety of algorithms is available to the skilled worker for comparing different sequences. In this context, the algorithms of Needleman and Wunsch or Smith and Waterman give particularly reliable results. To carry out the sequence alignments, the program PileUp (J. Mol. Evolution. 25, 351-360, 1987, Higgins et al., CABIOS, 5 1989: 151-153) or the programs Gap and BestFit (Needleman and Wunsch (J. Mol. Biol. 48; 443-453 (1970)) and Smith and Waterman (Adv. Appl. Math. 2; 482-489 (1981))), which are part of the GCG software packet (Genetics Computer Group, 575 Science Drive, Madison, Wisconsin, USA 53711 (1991)), are to be used. The sequence identity values recited above in percent (%) are to be determined, preferably, using the program GAP over the entire sequence region with the following settings: Gap Weight: 50, Length Weight: 3, Average Match: 10.000 and Average Mismatch: 0.000, which, unless otherwise specified, shall always be used as standard settings for sequence alignments.

A polynucleotide comprising a fragment of any of the specifically indicated nucleic acid sequences is also encompassed as a variant polynucleotide of the present invention. The fragment shall still the activity or encode a polypeptide still having the activity as specified. Accordingly, the polypeptide encoded may comprise or consist of the domains of the inhibitory polypeptide of the present invention conferring the said biological activity. A fragment as meant herein, preferably, comprises at least 50, at least 100, at least 250 or at least 500 consecutive nucleotides of any one of the specific nucleic acid sequences or encodes an amino acid sequence comprising at least 20, at least 30, at least 50, at least 80, at least 100 or at least 150 consecutive amino acids of any one of the specific amino acid sequences. The polynucleotide of the present invention shall be provided, preferably, either as an isolated polynucleotide (i.e. isolated from its natural context) or in genetically modified form. The polynucleotide, preferably, is DNA, including cDNA, or RNA. The term encompasses single as well as double stranded polynucleotides. Moreover, preferably, comprised are also chemically modified polynucleotides including naturally occurring modified polynucleotides such as glycosylated or methylated polynucleotides or artificial modified one such as biotinylated polynucleotides.

The polynucleotides of the present invention either consist, essentially consist of, or comprise the aforementioned nucleic acid sequences. Thus. they may contain further nucleic acid sequences as well. Specifically, the polynucleotides of the present invention may encode fusion proteins wherein one partner of the fusion protein is a polypeptide being encoded by a nucleic acid sequence recited above. Also, the polynucleotide may be comprised in a vector.

The term "vector", preferably, encompasses phage, plasmid, viral or retroviral vectors as well artificial chromosomes, such as bacterial or yeast artificial chromosomes. Moreover, the term also relates to targeting constructs which allow for random or site-directed integration of the targeting construct into genomic DNA. Such target constructs, preferably, comprise DNA of sufficient length for either homologous or heterologous recombination as described in detail below. The vector encompassing the polynucleotide of the present invention, preferably, further comprises selectable markers for propagation and/or selection in a host. The vector may be incorporated into a host cell by various techniques well known in the art. For example, a plasmid vector can be introduced in a precipitate such as a calcium phosphate precipitate or rubidium chloride precipitate, or in a complex with a charged lipid or in carbon-based clusters, such as fullerenes. Alternatively, a plasmid vector may be introduced by heat shock or electroporation techniques. Should the vector be a virus, it may be packaged in vitro using an appropriate packaging cell line prior to application to host cells. Retroviral vectors may be replication competent or replication defective. In the latter case, viral propagation generally will occur only in complementing host/cells. More preferably, in the vector of the invention the polynucleotide is operatively linked to expression control sequences allowing expression in prokaryotic or eukaryotic cells or isolated fractions thereof i.e. preferably, the polynucleotide is comprised in an expression vector. Expression of said polynucleotide comprises transcription of the polynucleotide into an RNA, preferably as specified above. Regulatory elements ensuring expression in eukaryotic cells, preferably mammalian cells, are well known in the art. They, preferably, comprise regulatory sequences ensuring initiation of transcription and, optionally, poly-A signals ensuring termination of transcription and stabilization of the transcript. Additional regulatory elements may include transcriptional as well as translational enhancers. Possible regulatory elements permitting expression in prokaryotic host cells comprise, e.g., the lac, trp or tac promoter in *E. coli*, and examples for regulatory elements permitting expression in eukaryotic host cells are the AOX1 or GAL1 promoter in yeast or the CMV-, SV40-, RSV-promoter (Rous sarcoma virus), CMV-enhancer, SV40-enhancer or a globin intron in mammalian and other animal cells. Moreover, inducible expression control sequences may be used in an expression vector encompassed by the present invention. Such inducible vectors may comprise tet or lac operator sequences or sequences inducible by heat shock or other environmental factors. Suitable expression control sequences are well known in the art. Beside elements which are responsible for the initiation of transcription such regulatory elements may also comprise transcription termination signals, such as the SV40-poly-A site or the tk-poly-A site, downstream of the polynucleotide. In this context, suitable expression vectors are known in the art such as Okayama-Berg cDNA expression vector pcDV1 (Pharmacia), pBluescript (Stratagene), pCDM8, pRc/CMV, pcDNA1, pcDNA3 (InVitrogene) or pSPORT1 (GIBCO BRL). Preferably, said vector is an expression vector and a gene transfer or targeting vector. Expression vectors derived from viruses such as retroviruses, vaccinia virus, adeno-associated virus, herpes viruses, or bovine papilloma virus, may be used for delivery of the polynucleotides or vector of the invention into targeted cell population. Methods which are well known to those skilled in the art can be used to construct recombinant viral vectors; see, for example, the techniques described in Sambrook, Molecular Cloning A Laboratory Manual, Cold Spring Harbor Laboratory (1989) N.Y. and Ausubel, Current Protocols in Molecular Biology, Green Publishing Associates and Wiley Interscience, N.Y. (1994).

Preferably, the Usp22 inhibitor is a small molecule inhibitor of Usp22, i.e. a chemical compound inhibiting Usp22 having a molecular mass of less than 5 kDa, preferably less than 2 kDa, most preferably less than 1 kDa. Preferably, the small molecule Usp22 inhibitor is a direct Usp22 inhibitor. Preferred small molecule Usp22 inhibitors are PR-619 and HBX 41108.

Preferably, the Usp22 inhibitor is comprised in a composition, preferably in a pharmaceutical composition.

The term "composition", as used herein, relates to a composition of matter comprising the compound as specified and optionally one or more acceptable carrier(s). Preferably, the composition is a pharmaceutic composition; thus, the composition, preferably, comprises the compound as specified as pharmaceutically active compound, and, preferably, the carrier is a pharmaceutically acceptable carrier. The pharmaceutically active compound can be formulated as, preferably pharmaceutically acceptable, salt. As used herein the term "pharmaceutically acceptable salts" refers to addition salts of these compounds with acids or bases that form anions or cations, which are, preferably, non-toxic to the recipient thereof. Examples of acid addition salts include acetate, adipate, ascorbate, benzoate, benzenesulfonate, bicarbonate, bisulfate, butyrate, camphorate, camphorsulfonate, choline, citrate, cyclohexyl sulfamate, diethylenediamine, ethanesulfonate, fumarate, glutamate, glycolate, hemisulfate, 2 -hydroxyethylsulfonate, heptanoate, hexanoate, hydrochloride, hydrobromide, hydroiodide, hydroxymaleate, lactate, malate, maleate, methanesulfonate, meglumine, 2-naphthalenesulfonate, nitrate, oxalate, pamoate, persulfate, phenylacetate, phosphate, diphosphate, picrate, pivalate, propionate, quinate, salicylate, stearate, succinate, sulfamate, sulfanilate, sulfate, tartrate, tosylate (p-toluenesulfonate), trifluoroacetate, and undecanoate salts. Examples of base addition salts include ammonium salts; alkali metal salts such as sodium, lithium and potassium salts; alkaline earth metal salts such as aluminum, calcium and magnesium salts; salts with organic bases such as dicyclohexylamine salts and N-methyl-D-glucamine; and salts with amino acids such as arginine, lysine, ornithine, and so forth. Also, basic nitrogen-containing groups may be quaternized with such agents as: lower alkyl halides, such as methyl, ethyl, propyl, and butyl halides; dialkyl sulfates such as dimethyl, diethyl, dibutyl; diamyl sulfates; long chain halides such as decyl, lauryl, myristyl and stearyl halides; arylalkyl halides such as benzyl bromide and others. The composition comprises at least one compound as indicated; thus, the composition preferably comprises one compound as specified or comprises a multitude of compounds, the term "multitude", preferably referring to at least two.

Preferably, the composition is a pharmaceutical composition, i.e., preferably, a medicament. The terms "medicament" and "pharmaceutical composition" are, in principle, known to the skilled person. As referred to herein, the terms relate to any composition containing a Usp22 inhibitor as pharmaceutically active compound and one or more other components such as one or more pharmaceutically acceptable carrier(s) and/or further pharmaceutically active compounds. The pharmaceutically active compound(s) can be present in liquid or dry, e.g. lyophilized, form. For example, the pharmaceutically active compound can be present together with glycerol and/or stabilizers (e.g., reducing agents, human serum albumin). The medicament is, typically, administered systemically or topically, preferably orally, by inhalation, or parenterally, e.g. by intravenous administration; however, preferably, subcutaneous or intramuscular administration may also be envisaged. However, depending on the nature of the formulation and the desired therapeutic application, the medicament may be administered by other routes as well. The pharmaceutically active compound is the active ingredient or drug of the medicament, and is preferably administered in conventional dosage forms prepared by combining the drug with standard pharmaceutical carriers according to conventional procedures. These procedures may involve mixing, granulating, and compression, or dissolving the ingredients as appropriate to the desired preparation. It will be appreciated that the form and character of the pharmaceutical acceptable carrier or diluent is dictated by the amount of active ingredient with which it is to be combined, the route of administration, and other well-known variables. The carrier(s) must be acceptable in the sense of being compatible with the other ingredients of the formulation and being not deleterious to the recipient thereof. The pharmaceutical carrier employed may include a solid, a gel, or a liquid. Exemplary of solid carriers are lactose, terra alba, sucrose, talc, gelatin, agar, pectin, acacia, magnesium stearate, stearic acid and the like. Exemplary of liquid carriers are phosphate buffered saline solution, syrup, oil, water, emulsions, various types of wetting agents, and the like. Similarly, the carrier or diluent may include time delay material well known to the art, such as glyceryl mono-stearate or glyceryl distearate alone or with a wax. Said suitable carriers comprise those mentioned above and others well known in the art, see, e.g., Remington's Pharmaceutical Sciences, Mack Publishing Company, Easton, Pennsylvania. The diluent(s) is/are selected so as not to affect the biological activity of the combination. Examples of such diluents are distilled water, physiological saline, Ringer's solutions, dextrose solution, and Hank's solution. In addition, the pharmaceutical composition or formulation may also include other carriers, adjuvants, or non-toxic, non-therapeutic, non-immunogenic stabilizers and the like. The medicament referred to herein is, preferably, administered at least once, e.g. as a bolus. However, the said medicament may be administered more than one time and, preferably, at least twice, e.g. permanently or periodically after defined time windows.

As used herein, the term "host cell" relates to any cell comprising a H2B and a Usp22. More preferably, the host cell is capable of modulating gene expression as an interferon response. Preferably, the cell is a eukaryotic cell, preferably a yeast cell, e.g. a cell of a strain of baker's yeast, or is an animal cell. More preferably, the host cell is an animal cell, preferably an insect cell or a mammalian cell, in particular a mouse or rat cell. Most preferably, the host cell is a human cell. As used herein, the term “target cell” relates to a host cell in which it is intended to modulate gene expression, in particular as an interferon-response.

The term “activation of the immune response”, as used herein, relates to the activation, i.e. preferably, increase in extent, of any response of an immune system of a subject to a self or non-self antigen, preferably to a non-self, a tumor, or other disease antigen. Thus, preferably, activation of an immune response comprises eliciting, enhancing, and/or prolonging an immune response. The immune system may be the innate immune system, preferably, is a pattern recognition mechanisms such as Toll-like receptors, and/or non-adaptive cellular response, such as activation of phagocytes, dendritic cells, and/or granulocytes. More preferably the immune system is the adaptive immune system, preferably cell-mediated immunity, e.g. mediated by T-cells and/or B-cells. Preferably, the activation of the immune response is activation of an interferon response, i.e. preferably, activation of genes which are activated by an interferon in the body of a subject. Preferably, the interferon response is an interferon-alpha and/or interferon-gamma response, preferably measured in hematopoietic stem cells, hematopoietic progenitor cells, pro-B cells, or pre-B cells. Preferably, activation of the immune response causes modulation, preferably activation, of at least one, preferably at least ten, more preferably at least 100 genes as shown in Table 1 herein below. Preferably, activation of the immune response as referred to herein causes a myeloid bias, i.e. a relative increase of white blood cells of the myeloid lineage over white blood cells of the lymphoid lineage. More preferably, a myeloid bias comprises a relative increase of immature granulocytes, monocytes, and/or macrophages, and/or a relative decrease of B-cells. Methods for determining myeloid bias are shown herein in the Examples.

Preferably, an immune response is activated in a vaccination of a subject. Thus, the Usp22 inhibitor may be for use in a vaccination of a subject. Thus, the Usp22 inhibitor may be administered preceding, concomitant to, or after a vaccination; as the skilled person will understand, if the Usp22 inhibitor is administered preceding or after a vaccination, it is preferably administered within a time period such that the activation of the immune response enhances vaccination. Thus, the Usp22 inhibitor is preferably administered within 2 weeks, preferably within 1 week, more preferably within 3 days, most preferably within one day of the vaccination. More preferably, the Usp22 inhibitor is administered concomitantly to the vaccination, preferably in a formulation for simultaneous administration, more preferably in a pharmaceutical composition comprising the vaccine and the Usp22 inhibitor. Thus, the Usp22 inhibitor preferably is used as an adjuvant in a vaccination. Preferably, in each of the aforesaid cases, the Usp22 inhibitor is administered at the same site as the vaccine or at a location less than 20 cm, preferably less than 10 cm, more preferably less than 5 cm within the vaccination site.

The term “subject”, as used herein, relates to an animal, preferably a vertebrate, more preferably a mammal, in particular to livestock like cattle, horse, pig, sheep, and goat, or to a laboratory animal like a rat, mouse, and guinea pig. Most preferably, the subject is a human. Preferably, the subject is in need for an activation of an immune response, more preferably in need of treatment and/or prevention of a virus infection, of a bacterial infection, of an autoimmune disease, or of cancer, all as specified elsewhere herein. Preferably, the subject is at increased risk of developing one or more of the aforesaid diseases. More preferably, the subject is known to suffer and/or is under treatment for one or more of the aforesaid diseases.

The terms “treating” and “treatment” refer to an amelioration of a disease or disorder referred to herein or the symptoms accompanied therewith to a significant extent; as used herein, the term includes prevention of deterioration of a disease, disorder, or symptoms associated therewith. Said treating as used herein also includes an entire restoration of health with respect to the diseases or disorders referred to herein. It is to be understood that treating, as the term is used herein, may not be effective in all subjects to be treated. However, the term shall require that, preferably, a statistically significant portion of subjects suffering from a disease or disorder referred to herein can be successfully treated. Whether a portion is statistically significant can be determined without further ado by the person skilled in the art using various well known statistic evaluation tools, e.g., determination of confidence intervals, p-value determination, Student’s t-test, Mann-Whitney test etc. Preferred confidence intervals are at least 90%, at least 95%, at least 97%, at least 98% or at least 99%. The p-values are, preferably, 0.1, 0.05, 0.01, 0.005, or 0.0001. Preferably, the treatment shall be effective for at least 10%, at least 20% at least 50% at least 60%, at least 70%, at least 80%, or at least 90% of the subjects of a given cohort or population. Preferably, treating comprises activating an immune response against an agent causing or mediating disease, i.e. against a virus and/or a host cell infected by said virus in case of a virus infection, against a bacterial cell and/or a host cell comprising a bacterial gene product in case of a bacterial infection, against a specific type of B-cell or other host cell causing or mediating disease in case of an autoimmune disease, or against a neoplastic cell, preferably a cancer cell in the case of cancer. Preferably, treating cancer is reducing tumor burden in a subject. As will be understood by the skilled person, effectiveness of treatment of e.g. cancer is dependent on a variety of factors including, e.g. cancer stage and cancer type.

The term “preventing” refers to retaining health with respect to the diseases or disorders referred to herein for a certain period of time in a subject. It will be understood that the said period of time may be dependent on the amount of the drug compound which has been administered and individual factors of the subject discussed elsewhere in this specification. It is to be understood that prevention may not be effective in all subjects treated with the compound according to the present invention. However, the term requires that, preferably, a statistically significant portion of subjects of a cohort or population are effectively prevented from suffering from a disease or disorder referred to herein or its accompanying symptoms. Preferably, a cohort or population of subjects is envisaged in this context which normally, i.e. without preventive measures according to the present invention, would develop a disease or disorder as referred to herein.

Whether a portion is statistically significant can be determined without further ado by the person skilled in the art using various well known statistic evaluation tools discussed elsewhere in this specification.

The term “virus infection” is understood by the skilled person. Preferably, the virus infection is an infection with a virus pathogenic to the subject. Preferably the virus is a hepadnavirus, a herpesvirus, a papillomavirus. Preferably, the virus is hepatitis virus, more preferably is hepatitis B virus or hepatitis C virus.

The term “bacterial infection” is understood by the skilled person as well. Preferably, the bacterial infection is an infection with a bacterium pathogenic to the subject. Preferably, the bacterium is *Mycobacterium tuberculosis* or *Listeria monocytogenes*.

The term "autoimmune disease" as used herein, relates to any and all disease in which the immune system of the subject reacts to a self-antigen and thereby causes disease. Preferably, the autoimmune disease is a disease treatable and/or preventable by interferon therapy. More preferably, the autoimmune disease is multiple sclerosis.

The term "cancer", as used herein, relates to a disease of a subject, characterized by uncontrolled growth by a group of body cells ("cancer cells"). This uncontrolled growth may lead to tumor formation and may be accompanied by intrusion into and destruction of surrounding tissue (invasion) and possibly spread of cancer cells to other locations in the body (metastasis). Preferably, also included by the term cancer is a relapse. Thus, preferably, the cancer is a non-solid cancer, a solid cancer, a metastasis, and/or a relapse thereof. Preferably, the cancer is characterized by local or systemic immune suppression, i.e. preferably, the cancer is not recognized by the subject's immune system. Preferably, cancer treatment comprises immunotherapy, preferably cell based immunotherapy. The term "immunotherapy", as used herein, relates to the treatment of cancer by modulation of the immune response of a subject. Said modulation may be inducing, enhancing, or suppressing said immune response, e.g. by administration of an Usp22 inhibitor and, optionally, additionally of at least one cytokine, and/or of at least one antibody specifically recognizing cancer cells. The term "cell based immunotherapy" relates to a cancer therapy comprising application of immune cells, e.g. T-cells, preferably tumor-specific NK cells, to a subject. Also preferably, cancer treatment further comprises at least one of surgery, chemotherapy, and radiotherapy.

Advantageously, it was found in the work underlying the present invention that decreasing Usp22 activity in a cell or a subject leads to induction of an immune response having the characteristics of an interferon response without requiring administration of interferon. Notably, the results described in this specification were recently confirmed in a viral infection model (Karlowitz et al. (2022), bioRxiv preprint doi.org/10.1101/2022.02.01.478628).

The definitions made above apply mutatis mutandis to the following. Additional definitions and explanations made further below also apply for all embodiments described in this specification mutatis mutandis.

The present invention further relates to a kit comprising a Usp22 inhibitor comprised in a housing.

The term "kit", as used herein, refers to a collection of the aforementioned compounds, means or reagents, which may or may not be packaged together. Preferably, the Usp22 inhibitor is comprised in a composition, preferably as a medicament, in the kit. The housing may be any kind of container and/or packaging deemed appropriate by the skilled person. The components of the kit may be comprised by separate vials (i.e. as a kit of separate parts) or provided in a single vial. Moreover, it is to be understood that the kit, preferably, is to be used for practicing the methods referred to elsewhere herein. It is, preferably, envisaged that all components are provided in a ready-to-use manner for practicing the methods referred to above. Further, the kit, preferably, contains instructions for carrying out said methods. The instructions can be provided by a user's manual in paper or electronic form. In addition, the manual may comprise instructions for administration and/or dosage instructions for carrying out the aforementioned methods using the kit of the present invention. Preferably, the kit comprises a diluent and/or a means of administration. Appropriate diluents are known to the skilled person; means of administration are all means suitable for administering the Usp22 inhibitor to a subject. The means of administration may include a delivery unit for the administration of the compound and a storage unit for storing said compound until administration. However, it is also contemplated that the means of the current invention may appear as separate devices in such an embodiment and are, preferably, packaged together in said kit. Preferred means for administration are those which can be applied without the particular knowledge of a specialized technician. In a preferred embodiment, the means for administration is a syringe, more preferably with a needle, comprising the compound or composition of the invention. In another preferred embodiment, the means for administration is an intravenous infusion (IV) equipment comprising the compound or composition. In still another preferred embodiment the means for administration is an inhaler comprising the compound of the present invention, wherein, more preferably, said compound is formulated for administration as an aerosol.

The present invention also relates to a method for identifying a subject susceptible to treatment of disease by administration of a Usp22 inhibitor comprising a) determining in a sample of said subject the amount and/or activity of a Usp22 gene product, of monoubiquitinated H2B (H2Bub1), and/or of a Usp22-modulated gene,
b) comparing said amount determined in step a) to a reference, and
c) based on the result of step b), identifying a subject susceptible to treatment of disease by administration of a Usp22 inhibitor.

The method for identifying a subject, preferably, is an in vitro method. Moreover, it may comprise steps in addition to those explicitly mentioned above. For example, further steps may relate, e.g., to providing a sample for step a), or providing treatment, e.g. treatment with an Usp22 inhibitor if the subject is identified to be susceptible to such treatment in step c). Preferably, the method comprises determining the amount and/or activity of a Usp22 gene product, of monoubiquitinated H2B (H2Bub1), and/or of at least one, preferably at least 10, more preferably at least 100, Usp22-modulated gene(s).

As used herein, the term "susceptible to treatment of disease by administration of a Usp22 inhibitor" relates to a subject having an insufficient or absent immune response, preferably insufficient or absent interferon response, preferably in response to a disease as specified herein.

Thus, preferably, the subject susceptible to treatment of disease by administration of a Usp22 inhibitor is in need of an activation of an interferon response.

The term "sample" refers to a sample of separated cells or to a sample from a tissue or an organ. Tissue or organ samples may be obtained from any tissue or organ by, e.g., biopsy. Separated cells may be obtained from the body fluids, such as lymph, blood, plasma, serum, liquor and other, or from the tissues or organs by separating techniques such as centrifugation or cell sorting. Preferably, the sample is a tissue or body fluid sample which comprises cells.

Preferably the sample is a sample of a body fluid, preferably a blood sample. The sample can be obtained from the subject by routine techniques which are well known to the person skilled in the art, e.g., venous or arterial puncture or open biopsy including aspiration of tissue or cellular material from a subject. For those areas which cannot be easily reached via an open biopsy, a surgery and, preferably, minimal invasive surgery can be performed.

The term "Usp22-modulated gene" is understood by the skilled person. Preferably, the term includes any and all genes whose expression changes compared to a control in a host cell if Usp22 activity in said host cell is decreased or, preferably, abolished. Preferably, the Usp22-modulated gene is selected from the genes indicated in Table 1, preferably is an immune-related gene of Table 1, more preferably is a non-immune-related gene of Table 1. As is understood by the skilled person in view of the disclosure herein, the Usp22-modulated gene preferably is an interferon-modulated gene.

The term "gene product", as used herein, includes any and all products of a gene if expressed, including fragments and derivatives of said products. Thus, the gene product preferably is an RNA, more preferably an mRNA, or a derivative or fragment thereof; or a polypeptide, or a derivative or fragment thereof. As the skilled person understands, the amount of a polynucleotide gene product is preferably determined by methods involving hybridization of one or more specific oligonucleotide(s), e.g. PCR primers and/or oligonucleotide probes, to polynucleotides obtained from a sample; appropriate methods are known in the art. Also, determination of the amount of a polypeptide may be achieved by any method deemed appropriate by the skilled person, e.g. by methods involving binding of an antibody. Determining the activity of a gene product, as the skilled person understands, depends on the gene whose product is to be determined, as is also understood by the skilled person, typically the activity of a polypeptide gene product, in particular an enzymatic activity, is determined. E.g. the activity of the Usp22 gene product can be determined by determining the enzymatic Usp22 activity in a sample. More preferably, the amount of H2Bub1 present in the sample is determined as a surrogate marker of Usp22 activity. Preferably, for Usp22-modulated genes for which the activity is not known or cannot be reliably determined, the amount of at least one gene product is determined.

The term "reference", as used herein, refers to a value of the Usp22 gene product, of monoubiquitinated H2B (H2Bub1), and/or of an interferon-stimulated gene in a reference cell. Preferably, a reference is a threshold value (e.g., an amount or ratio of amounts) for a gene product. The reference may, however, also be a value derived from an amount by any mathematical deemed appropriate by the skilled person, in particular normalization. In accordance with the aforementioned method, a reference is, preferably, a reference obtained from a sample from a subject or group of subjects known to be susceptible to treatment by administration of a Usp22 inhibitor. In such a case, a value for the gene product found in a sample being essentially identical to said reference is indicative for the subject to be susceptible to treatment by administration of a Usp22 inhibitor. Also preferably, the reference is from a subject or group of subjects known not be susceptible to treatment by administration of a Usp22 inhibitor, i.e. preferably, an apparently healthy subject or group thereof. In such a case, a value for the gene product(s) found in the test sample being altered with respect to the reference is indicative for the subject being susceptible to treatment by administration of a Usp22 inhibitor. The same applies mutatis mutandis for a calculated reference, most preferably the average or median, for the relative or absolute value of the at gene product(s) of a population of individuals, optionally comprising the subject to be investigated. The absolute or relative values of the at least gene product can be determined by methods known in the art. How to calculate a suitable reference value, preferably, the average or median, is well known in the art. The population of subjects referred to before shall comprise a plurality of subjects, preferably, at least 5, 10, 50, 100, 1,000 or 10,000 subjects. It is to be understood that the subject to be diagnosed by the method of the present invention and the subjects of the said plurality of subjects preferably are of the same species. The value for the at least one gene product of the test sample and the reference values are essentially identical if the corresponding values are essentially identical. Essentially identical means that the difference between two values is, preferably, not significant and shall be characterized in that the values are within at least the interval between 1st and 99th percentile, 5th and 95th percentile, 10th and 90th percentile, 20th and 80th percentile, 30th and 70th percentile, 40th and 60th percentile of the reference value, preferably, the 50th, 60th, 70th, 80th, 90th or 95th percentile of the reference value. Statistical test for determining whether two amounts are essentially identical are well known in the art. An observed difference for two values, on the other hand, shall be statistically significant. A difference in the relative or absolute value is, preferably, significant outside of the interval between 45th and 55th percentile, 40th and 60th percentile, 30th and 70th percentile, 20th and 80th percentile, 10th and 90th percentile, 5th and 95th percentile, 1st and 99th percentile of the reference value. Preferably, the reference(s) are stored in a suitable data storage medium such as a database and are, thus, also available for future assessments.

The present invention also relates to a medicament for treating and/or preventing cancer or an infection comprising (i) a Usp22 inhibitor and (ii) a pharmaceutically acceptable carrier.

The instant invention also relates to a method for identifying a compound for activation of an immune response in a subject, comprising a) contacting a reaction mixture comprising a Ubiquitin-specific peptidase 22 and Histone 2B-ubiquitin conjugate (H2Bub1) with a compound suspected to have the activity of being an activator of said immune response,
b) determining the deubiquitination of H2Bub1 in the reaction mixture, and
c) identifying a compound for activation of an immune response based on the result of the determination step of b).

The term "reaction mixture" is understood by the skilled person and relates to any mixture providing appropriate conditions for Usp22 activity to occur, e.g. pH, ionic strength, presence of substrate, cofactors and ions, and the like. The assay components may be purified components, more preferably are non-purified or enriched fractions of said components. Thus, the reaction mixture may, preferably, also be the inside or an extract of a host cell.

The term "determining the deubiquitination of H2Bub1" relates to determination of any parameter correlating with the deubiquitination of H2Bub1. Depending on the assay, deubiquitination may e.g. be detected by a size shift of the H2Bub1 band to a lower molecular weight, or loss of an antigenic determinant, such as ubiquitin, from H2Bub1.

The term "compound suspected to have the activity of being an activator of said immune response" includes any and all compounds for which it may be assumed that they are activators of said immune response. Preferably, the compound is suspected to be a Usp22 inhibitor, more preferably a direct or indirect Usp22 inhibitor as specified herein above, more preferably is a low-molecular weight compound, preferably having a molecular weight of less than 5 kDa, preferably less than 2 kDa, most preferably less than 1 kDa, being a suspected Usp22 inhibitor.

The invention also relates to a method for identifying a compound for activation of an immune response in a subject, comprising (A) contacting a host cell with a compound suspected of being an activator of said immune response;

(B) determining the amount of H2Bub1 and/or of at least one H2Bub1 modulated gene of Table 1 in said cell;

(C) comparing the amount or amounts determined in step (B) to a reference or to references; and (D) identifying a compound for activation of an immune response in a subject based on the result of comparison step (C).

The reference in the method for identifying a compound, preferably, is derived from host cells not treated with a compound suspected of being an activator of the immune response; in such case, an amount of H2Bub1 and/or of at least one H2Bub1 modulated gene deviating from the reference preferably is indicative of a compound being an activator of said immune response; also preferably, the reference is derived from host cells treated with a compound known to be an activator of the immune response; in such case, an amount of H2Bub1 and/or of at least one H2Bub1 modulated gene similar or identical to the reference preferably is indicative of a compound being an activator of said immune response.

Also, the present invention relates to an in vivo method of identifying a compound for activation of an immune response and/or a Usp22 inhibitor in a subject comprising (I) contacting an experimental animal with a compound suspected to be a Usp22 inhibitor, (II) determining a parameter representative of the lymphoid cell count compared to the myeloid cell count in the blood of said experimental animal; and (III) identifying a compound for activation of an immune response if a myeloid bias is detected.

The skilled person is able to determine a parameter representative of the lymphoid cell count compared to the myeloid cell count, e.g. by counting cells, optionally after appropriate staining, or by FACS-sorting, optionally after staining blood cells, preferably white blood cells, for suitable surface markers. preferably, the parameter representative of the lymphoid cell count compared to the myeloid cell count is the lymphoid-to-myeloid ratio. Also preferably, the said experimental animal is sacrificed after step (ID or (HD.

In view of the above, the following embodiments are particularly envisaged:

Embodiment 1: An inhibitor of ubiquitin-specific peptidase 22 (Usp22 inhibitor) for use in activation of an immune response in a subject.

Embodiment 2: The Usp22 inhibitor for use of embodiment 1, wherein activation of an immune response comprises eliciting, enhancing, and/or prolonging the immune response.

Embodiment 3: The Usp22inhibitor for use of embodiment 1 or 2, wherein the activation of an immune response is activation of an interferon-response.

Embodiment 4: The Usp22 inhibitor for use of any one of embodiments 1 to 3, wherein the activation of an immune response is treatment and/or prevention of a virus infection, of a bacterial infection, of a fungal infection, of an autoimmune disease, or of cancer.

Embodiment 5: The Usp22 inhibitor for use of any one of embodiments 1 to 4, wherein said autoimmune disease is multiple sclerosis.

Embodiment 6: The Usp22 inhibitor for use of any one of embodiments 1 to 5, wherein said Usp22 inhibitor is a direct Usp22 inhibitor, preferably is a polypeptide, polynucleotide, or small molecule, specifically binding and inhibiting Usp22.

Embodiment 7: The Usp22 inhibitor for use of any one of embodiments 1 to 6, wherein said Usp22 inhibitor is selected from the list consisting of an antibody, an aptamer, an anticalin, and a Designed Ankyrin Repeat Protein (DARPin).

Embodiment 8: The Usp22 inhibitor for use of any one of embodiments 1 to 7, wherein said Usp22 inhibitor is an indirect Usp22 inhibitor, preferably is a polynucleotide.

Embodiment 9: The Usp22 inhibitor for use of any one of embodiments 1 to 8, wherein said Usp22 inhibitor is selected from the list consisting of a shRNA, a siRNA, a miRNA agent, an antisense molecule, an antisense oligonucleotide, a ribozyme, and a pair of CRISPR/Cas oligonucleotides.

Embodiment 10: A kit comprising a Usp22 inhibitor comprised in a housing.

Embodiment 11: A method for identifying a subject susceptible to treatment of disease by administration of a Usp22 inhibitor comprising a) determining in a sample of said subject the amount of a Usp22 gene product, of monoubiquitinated H2B (H2Bub1), and/or of an interferon-stimulated gene, b) comparing mid amount determined in step a) to a reference, and c) based on the result of step b), identifying a subject susceptible to treatment of disease by administration of a Usp22 inhibitor.

Embodiment 12: The method of embodiment 11, wherein said disease is a virus infection, a bacterial infection, an autoimmune disease, or a cancer.

Embodiment 13: A medicament for treating and/or preventing cancer or an infection comprising (i) a Usp22 inhibitor and (ii) a pharmaceutically acceptable carrier.

Embodiment 14: A method for identifying a compound for activation of an immune response in a subject, comprising a) contacting a reaction mixture comprising a Ubiquitin-specific peptidase 22 and Histone 2B-ubiquitin conjugate (H2Bub1) with a compound suspected to have the activity of being an activator of said immune response, b) determining the deubiquitination of H2Bub1 in the reaction mixture, and c) identifying a compound for activation of an immune response based on the result of the determination step of b).

Embodiment 15: A method for identifying a compound for activation of an immune response in a subject, comprising (A) contacting a host cell with a compound suspected of being an activator of said immune response;

(B) determining the amount of H2Bub1 and/or of at least one H2Bub1 modulated gene of Table 1 in said host cell;

(C) comparing the amount or amounts determined in step (B) to a reference or to references; and (D) identifying a compound for activation of an immune response in a subject based on the result of comparison step (C).

Embodiment 16: An in vivo method of identifying a compound for activation of an immune response and/or a Usp22 inhibitor in a subject comprising (I) contacting an experimental animal with a compound suspected to be a Usp22 inhibitor, (I) determining a parameter representative of the lymphoid cell count compared to the myeloid cell count in the blood of said experimental animal; and (III) identifying a compound for activation of an immune response if a myeloid bias is detected.

Embodiment 17: The method of embodiment 16, wherein said parameter representative of the lymphoid cell count compared to the myeloid cell count is the lymphoid-to-myeloid ratio.

Embodiment 18: The method of embodiment 16 or 17, wherein said experimental animal is sacrificed after step (H) or (I).

Embodiment 19: The method of any one of embodiments 16 to 18, wherein the immune response is an interferon-response.

All references cited in this specification are herewith incorporated by reference with respect to their entire disclosure content and the disclosure content specifically mentioned in this specification.

FIGURE LEGENDS

As will be understood by the skilled person, in all column graphs showing wt and ko columns, the wt columns are shown first (left) and the ko columns are shown second (right).

FIG. 1: Usp22 deficiency drives enhanced H2B monoubiquitination and ISG expression. (A) Quantitative reverse transcription (qRT-)PCR analysis for Usp22 mRNA expression in long-term (LT-) hematopoietic stem cells (HSC), short-term (ST-) HSC, multipotent progenitors (MPP) and common myeloid progenitors (CMP) from bone marrow, and B cells, $CD4^+$ T cells, $CD8^+$ T calls and granulocytes from the spleens of wild type and Usp22KO mice (n=3–6). (B) Western Blot analysis for H2B and H2Bub1 in bone marrow hematopoietic stem and progenitor cells (HSPC), and splenic B ($CD19^+B220^+$), T (both $CD4^+$ and $CD8a^+$ cells) and myeloid cells ($CD11b^+$) from wild type and Usp22 KO mice. (C+D) Gene set enrichment analysis (GSEA) plots for IFNα target genes (C) and IFNγ target genes (D) Comparison of RNA sequencing data from wild type and Usp22KO HSPC. (E+F) qRT-PCR analysis for mRNA expression of Stat-1 (E) and Ifi47 (F) in wild type and Usp22 KO stem and progenitor populations (n=6). (G) Unaltered interferon serum levels in wild type and Usp22 KO mice (n=9-12). * $p<0.05$,  $p<0.01$, * $p<0.001$, **** $p<0.0001$.

Figure 2:
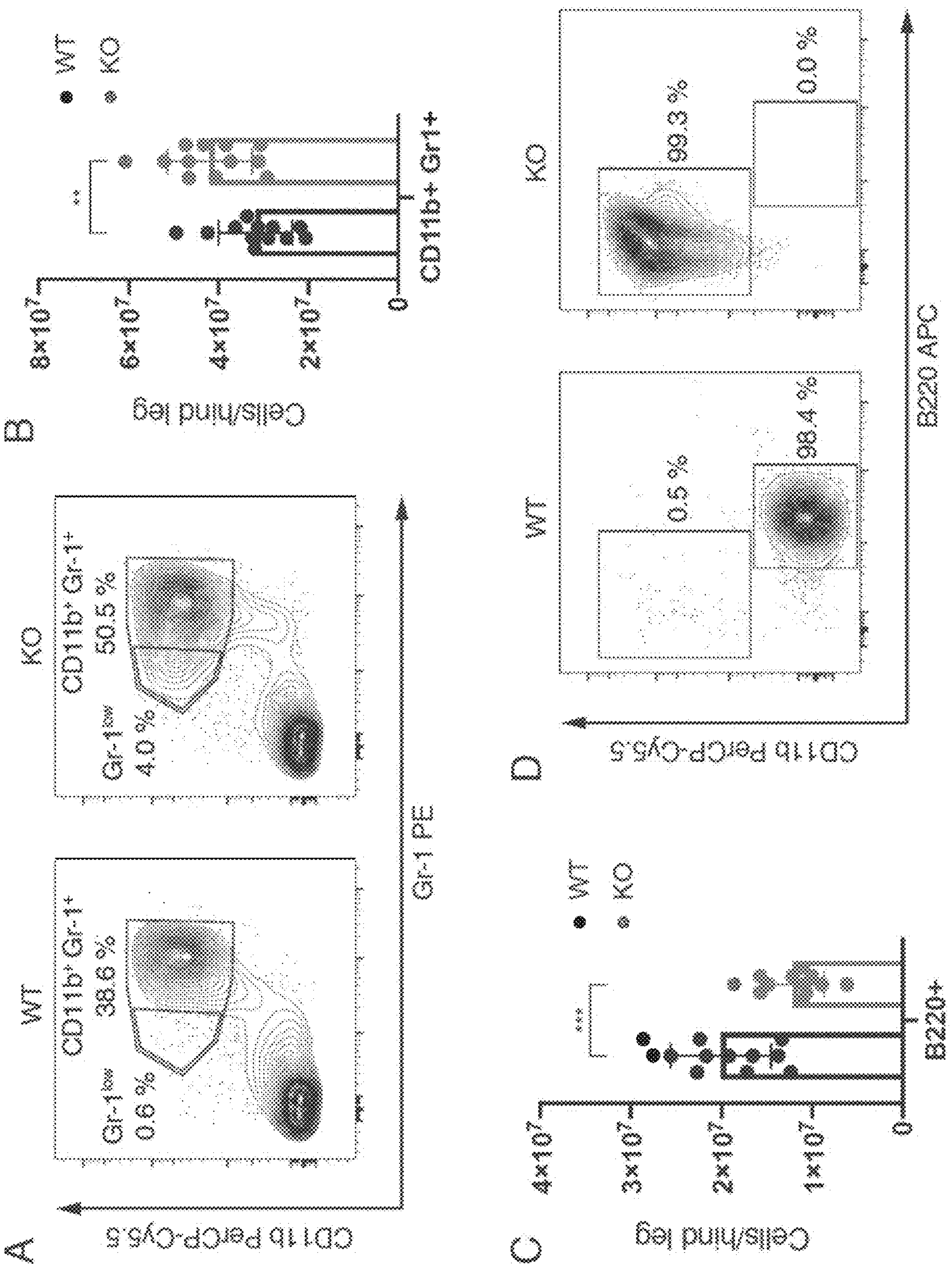
Figure 2:
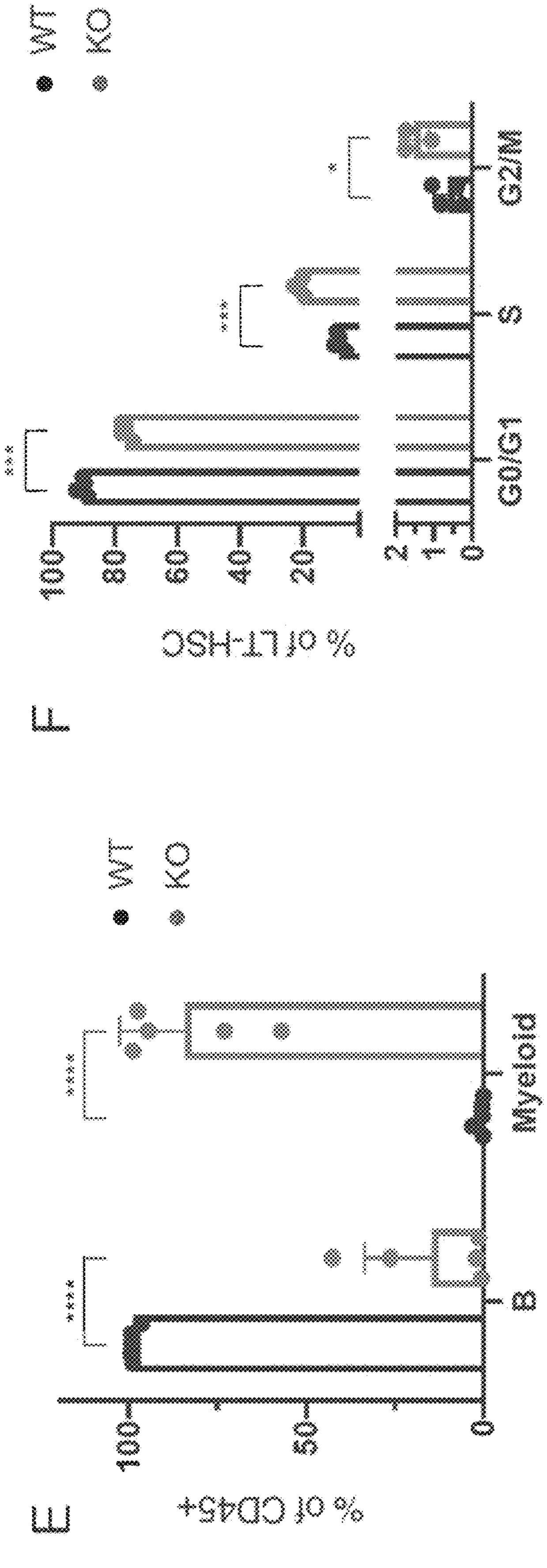

FIG. 2: Enhanced myeloid development and myeloid bias in Usp22 KO mice. (A) Flow cytometric analysis of wild type and Usp22 KO BM cells stained for CD11b and Gr-1. (B) Absolute numbers of $CD11b^+Gr^+$ myeloid cells in the bone marrow of wild type and Usp22KO mice (n=12). (C) Absolute numbers of B220* B cells in the bone marrow of wild type and Usp22 KO mice (n=12). (D) CD11b versus B220 expression 3 weeks after in vitro differentiation of wild type and Usp22 KO HSPC. (E) Relative proportions of $B220^+$ B cells and $CD11b^+$ myeloid cells (gated as shown in (D)) 3 weeks after in vitro differentiation of wild type or Usp22 KO HSPC. Each dot represents the mean of 3-5 replicates of progenitors from one donor mouse. Graph represents the results from 5 mice per genotype.(F) Cell cycle analysis of wild type and Usp22 KO LT-HSC based on EdU incorporation (n=3–4).* $p<0.05$,  $p<0.01$, * $p<0.001$, **** $p<0.0001$.

Figure 3:
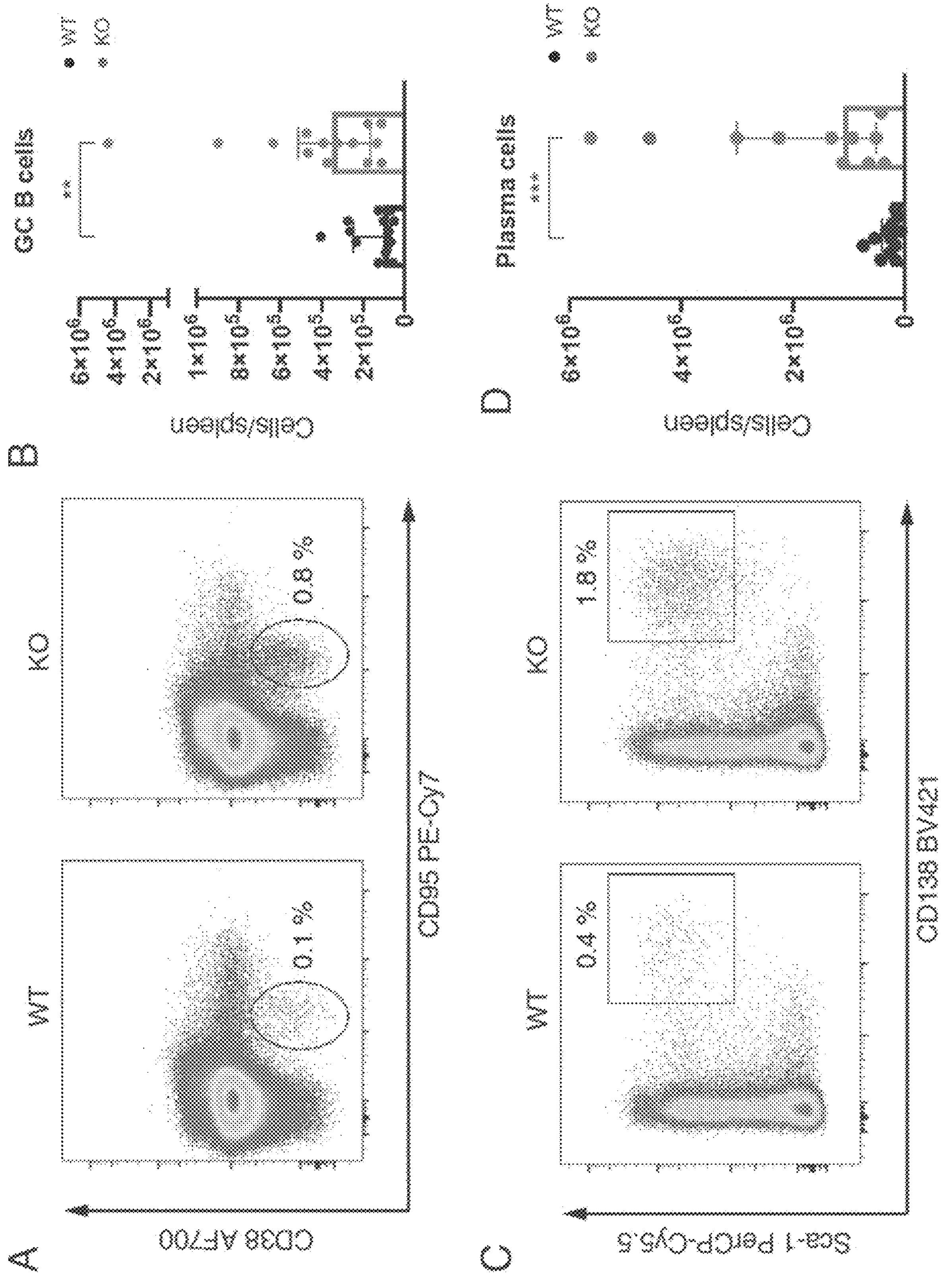
Figure 3:
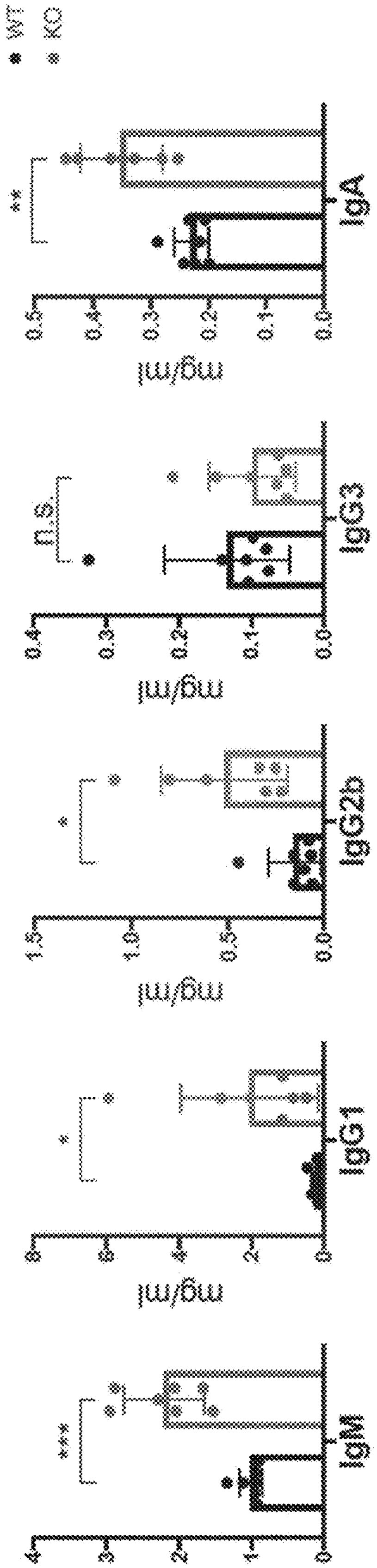

FIG. 3: Usp22 deficiency results in enhanced immunoglobulin production. (A) Percentages of $CD38^-CD95^+$ germinal center (GC) B cells (pre-gated on $CD19^+B220^+$ B cells) comparing wild type and Usp22 KO spleens. (B) Absolute numbers of GC B cells (n=13-14) in the spleens of wild type and Usp22 KO mice. (C) Percentages of $Sca-1^+$ $CD138^{high}$ plasma cells (PC) in wild type and Usp22 KO spleens. (D) Absolute numbers of plasma cells in spleens (n=11–12) of wild type and Usp22 KO mice. (E) Serum concentrations of the indicated immunoglobulin isotypes in wild type and Usp22 KO mice (n=7). * $p<0.05$,  $p<0.01$, * $p<0.001$, **** $p<0.0001$.

Figure 4:
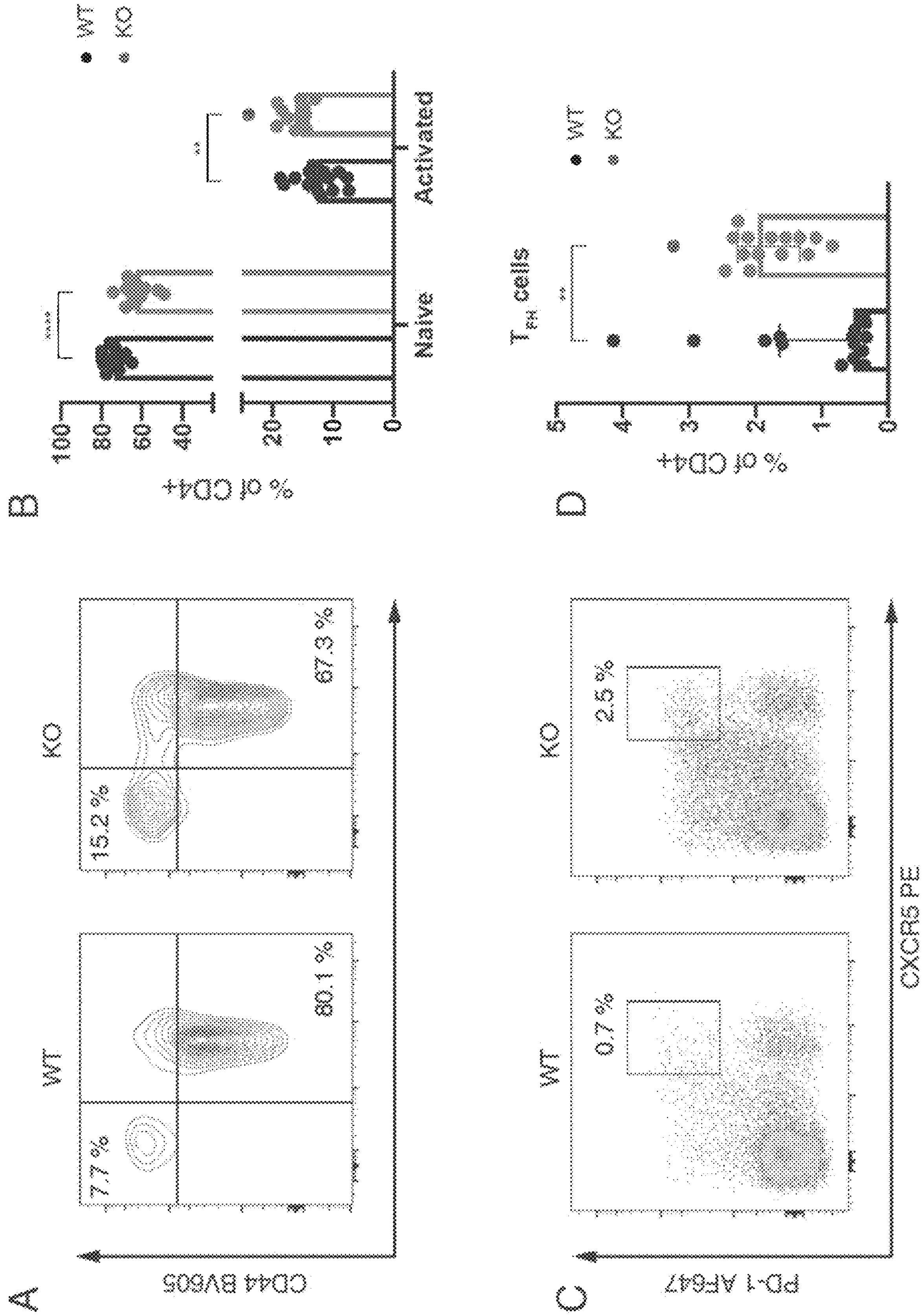

FIG. 4: Spontaneous T cell activation in Usp22-deficient mice. (A) Percentages of $CD62L^+CD44^{low}$ naïve and $CD62LCD44^{high}$ activated T cells (pre-gated on $CD3^+$ $CD4^+$) in wild type and Usp22KO spleens. (B) Relative proportions of naïve and activated $CD4^+$ T cells (gated as in (A)) in the spleens of wild type and Usp22 KO mice (n=15). (C) Percentages of $PD-1^+CXCR5^+$ T follicular helper ($T_{FH}$) cells (pre-gated on $CD3^+CD4^+$) in wild type and Usp22 KO spleens. (D) Percentages of $T_{FH}$ cells (gated as in (C)) within the splenic $CD4^+$ T cell populations of wild type and Usp22 KO mice (n=15). * $p<0.05$,  $p<0.01$, * $p<0.001$, **** $p<0.0001$.

Figure 5:
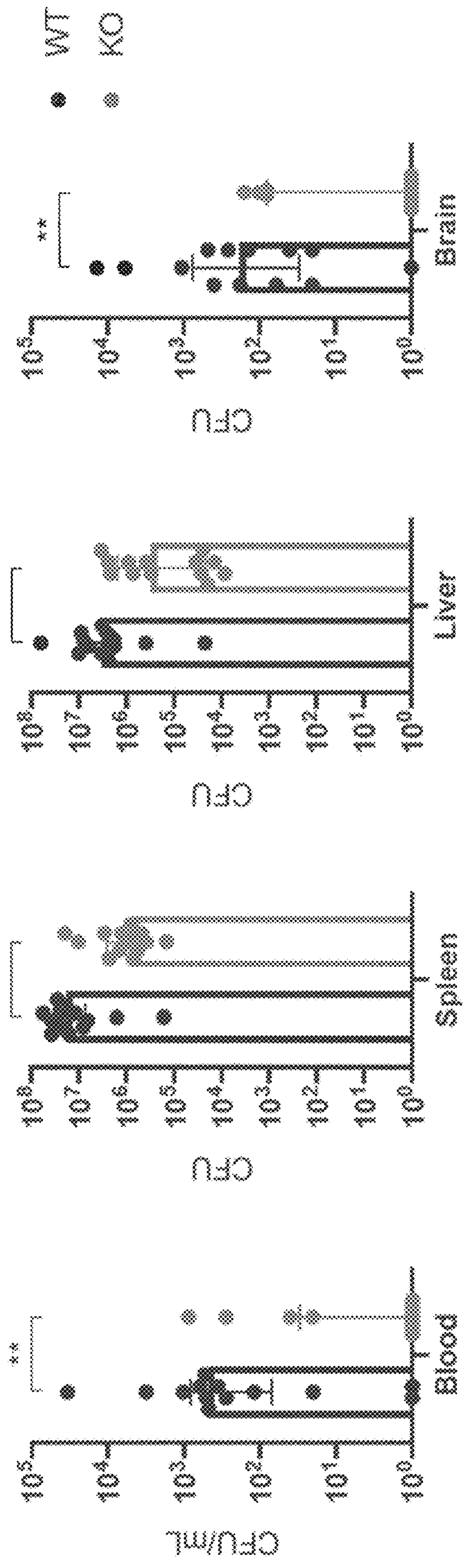

FIG. 5: Loss of Usp22 enhances protection against *Listeria monocytogenes* infection in mice. (A-D) *Listeria monocytogenes* colony-forming units (CFU) in blood (A), brain (B), liver (C) and spleen (D) of wildtype (black dots), and Usp22 KO (grey dots) mice three days after intravenous infection with $10^4$ CFU *Listeria monocytogenes* (n=13). ** $p<0.01$ by two-tailed Mann-Whitney test.

Figure 6:
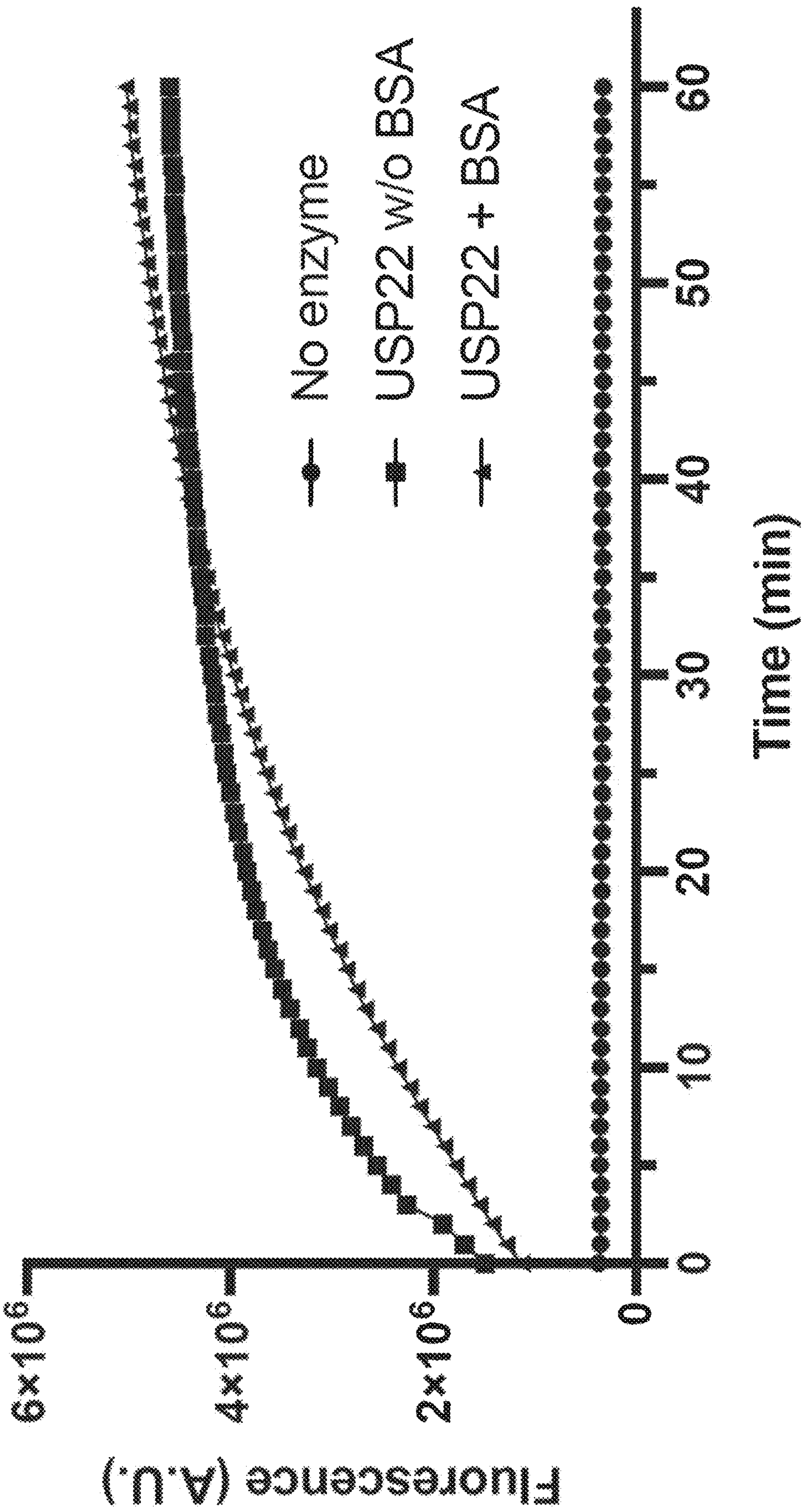

FIG. 6: Development of an in vitro assay to measure deubiquitinating activity of recombinant USP22. Time course analysis of the fluorescence signal generated by cleavage of the fluorogenic substrate AMC-Ubiquitin by recombinant USP22 in vitro using different reaction buffer formulations with (black triangles) or without bovine serum albumin (black squares). Background fluorescence (no enzyme) is shown as black circles. A.U.=arbitrary units.

The following Examples shall merely illustrate the invention. They shall not be construed, whatsoever, to limit the scope of the invention.

Example 1: Usp22 Regulates H2B Monoubiquitination and Interferon-Stimulated Gene (ISG) Expression in Hematopoietic Cells The inventors tested the hypothesis that enhanced H2B monoubiquitination might elicit increased ISG expression in hematopoietic cells. To this end, they generated pan-hematopoietic Usp22 knock-out mice (referred to as Usp22 KO mice throughout the text) by crossing Vav1-Cre mice with Usp22 flox mice. The resulting Usp22 KO mice showed strongly decreased Usp22 mRNA levels (FIG. 1A). Importantly, Usp22 deficiency led to enhanced H2B monoubiquitination in several cellular lineages of the hematopoietic system (FIG. 1B), showing that Usp22 acts as a non-redundant H2Bub1 deubiquitinase in hematopoietic cells. Consequently, Usp22 KO mice represent a good model to study the effects of altered H2Bub1 levels on ISG expression.

To explore the consequences of Usp22 deficiency on ISG expression, the inventors performed gene expression profiling of Usp22-deficient hematopoietic cells by RNA sequencing, using hematopoietic stem and progenitor cells (HSPC) as a model cell type. Genes found to be modulated by Usp22-inhibition are listed in Table 1 below. Gene set enrichment analysis revealed that Usp22-deficient cells express higher levels of type I and type H interferon target genes (FIG. 1C+D). These findings were further confirmed by quantitative real time PCR for the two prototypical ISG Stat-1 and Ifi-47 (FIG. 1E+F). Importantly, enhanced ISG expression in Usp22-deficient mice occurred despite the fact that interferon serum levels were not elevated (FIG. 1G), and no signs of infections or diseases were detectable (data not shown).

Collectively, the inventors' results demonstrate that Usp22 acts as a negative regulator of ISG expression in a cell-autonomous manner.

Example 2: Usp22 Deficiency Mimics Interferon Stimulation in Hematopoiesis In Vivo Given the above described role of Usp22 as a negative regulator of ISG expression in hematopoietic cells, the inventors hypothesized that Usp22 KO mice would show typical phenotypes of interferon stimulation, such as enhanced myelopoiesis, impaired B cell development, and cell cycle activation of hematopoietic stem cells (HSC). To test this idea, the inventors performed immune cell phenotyping in Usp22 KO mice.

Usp22 KO mice showed increased numbers of $CD11b^+$ myeloid cells (FIG. 2A+B) and an accumulation of immature myeloid cells characterized by low expression of Gr−1 (FIG. 2A). While myelopoiesis was enhanced in the absence of Usp22, B cell development was impaired in Usp22 KO mice as shown by reduced numbers of $B220^+$ B cells in the bone marrow (FIG. 2C). By performing OP9 in vitro differentiation assays using undifferentiated HSPC from wild type and Usp22 KO mice as input, the inventors could further demonstrate that the imbalance between myeloid and lymphoid development (myeloid bias) persisted even under conditions favoring B cell development (FIG. 2D+E). Importantly, OP9 differentiation assays using mixed populations of wild type and Usp22 KO HSPC as input showed that the myeloid bias of Usp22 KO HSPC was neither reverted by the presence of wild type cells, nor was it transferable to wild type cells (data not shown), demonstrating that this phenotype is cell-intrinsic. Finally, EdU labeling experiments revealed enhanced proliferation of Usp22-deficient HSC (FIG. 2F). Taken together, these findings establish that Usp22 deficiency induces typical phenotypes associated with interferon stimulation in hematopoietic cells, further demonstrating the role of Usp22 as a negative regulator of the interferon response.

Example 3

Interferons can enhance B cell responses and antibody production as well as T cell activation. Therefore, the inventors next asked how Usp22 deficiency would affect the adaptive arm of the immune system. In agreement with their overall interferon response-like phenotype, Usp22 KO mice showed increased numbers of germinal center B cells (FIG. 3A+B) as well as of plasma cells in the spleens (FIG. 3C+D) and in the bone marrow (data not shown). Consistent with increased germinal center and plasma cell numbers, Usp22-deficient mice showed strongly elevated serum levels of most antibody (immunoglobulin) isotypes (FIG. 3E). Besides affecting the humoral part of the adaptive immune system, Usp22 deficiency led to enhanced activation of $CD4^+$ T cells in the spleen (FIG. 4A+B). In line with the aforementioned elevation of serum immunoglobulins, Usp22-deficient mice showed increased frequencies of splenic follicular T helper cells ($T_{FH}$ cells) (FIG. 4C+D).

In summary, loss of Usp22 phenocopies interferon-stimulated adaptive immunity and therefore inhibition of Usp22 might represent a new and effective means to activate and/or enhance an individual's immune response.

TABLE 1

Genes modulated by Usp22-inhibition.

| Gene Name | Genbank Acc No. | log2 fold change | p-value | adjusted p-value | immune-related |
|---|---|---|---|---|---|
| Crtam | NM_001281954.1 | 7.249615598 | 1.29E−19 | 3.83E−17 | yes |
| Xcl1 | NM_008510.1 | 5.583917662 | 4.37E−61 | 2.54E−57 | yes |
| Tnfrsf9 | NM_001077508.1 | 5.279889028 | 6.07E−33 | 5.42E−30 | yes |
| Klre1 | NM_001381986.1 | 4.990443917 | 1.94E−43 | 3.21E−40 | yes |
| Ncr1 | NM_010746.3 | 4.803007808 | 3.42E−43 | 4.96E−40 | yes |
| Cd160 | NM_001163496.1 | 4.754210872 | 1.72E−40 | 2.21E−37 | yes |
| Cd2 | NM_013486.2 | 4.634468982 | 6.66E−54 | 1.93E−50 | yes |
| Sh2d1a | NM_011364.4 | 4.073930401 | 9.56E−29 | 5.28E−26 | yes |
| Slamf7 | NM_144539.5 | 4.071559421 | 2.12E−19 | 5.71E−17 | yes |
| Klrg1 | NM_016970.1 | 4.04024846 | 9.71E−15 | 1.88E−12 | yes |
| Klrk1 | NM_033078.4 | 3.999634123 | 4.88E−31 | 3.33E−28 | yes |
| Ikzf3 | NM_011771.1 | 3.959182348 | 1.55E−08 | 1.52E−06 | yes |
| Klrc1 | NM_001136068.2 | 3.889453001 | 5.74E−22 | 2.15E−19 | yes |
| Il2rb | NM_008368.4 | 3.855720458 | 1.35E−17 | 3.13E−15 | yes |
| Gzma | NM_010370.2 | 3.733910485 | 9.67E−79 | 1.12E−74 | yes |
| Klrd1 | NM_010654.3 | 3.71031967 | 3.51E−27 | 1.70E−24 | yes |
| Cd3d | NM_013487.3 | 3.302155266 | 3.69E−22 | 1.48E−19 | yes |
| Txk | NM_001122754.2 | 3.29125186 | 1.75E−20 | 6.15E−18 | yes |
| Ifi205 | NM_172648.3 | 3.257959949 | 6.84E−20 | 2.14E−17 | yes |
| Prf1 | NM_011073.3 | 3.214188958 | 0.000120172 | 0.004859238 | yes |
| Ccl5 | NM_013653.3 | 3.204287312 | 3.44E−33 | 3.33E−30 | yes |
| Cd3g | NM_009850.2 | 3.116668332 | 4.69E−24 | 2.02E−21 | yes |
| Gzmm | NM_001302499.1 | 3.071077643 | 6.55E−20 | 2.11E−17 | yes |
| Cd200r2 | NM_206535.1 | 3.020636787 | 0.000135228 | 0.00539284 | yes |
| Klrblc | NM_001159904.1 | 2.770086701 | 2.72E−18 | 6.72E−16 | yes |
| Cd226 | NM_178687.2 | 2.734564798 | 9.07E−16 | 1.95E−13 | yes |
| Klrb1b | NM_030599.4 | 2.653657074 | 9.02E−14 | 1.69E−11 | yes |
| H2-Eb1 | NM_010382.2 | 2.600851636 | 2.87E−60 | 1.11E−56 | yes |
| Gzmb | NM_013542.2 | 2.552420659 | 3.04E−08 | 2.87E−06 | yes |
| Batf3 | NM_030060.2 | 2.478065225 | 3.00E−10 | 3.83E−08 | yes |
| Tigit | NM_001146325.1 | 2.436553776 | 2.16E−12 | 3.68E−10 | yes |

TABLE 1-continued

Genes modulated by Usp22-inhibition.

| Gene Name | Genbank Acc No. | log2 fold change | p-value | adjusted p-value | immune-related |
|---|---|---|---|---|---|
| Zap70 | NM_009539.3 | 2.307673048 | 0.00123154 | 0.034858579 | yes |
| Cd74 | NM_010545.3 | 2.23265808 | 3.42E−30 | 2.09E−27 | yes |
| H2-Aa | NM_010378.2 | 2.215874945 | 5.51E−50 | 1.28E−46 | yes |
| Cd28 | NM_007642.4 | 2.056538279 | 4.11E−11 | 6.19E−09 | yes |
| Ifi211 | NM_001033450.4 | 2.013335106 | 2.12E−15 | 4.32E−13 | yes |
| Mefv | NM_001161790.1 | 1.938251782 | 2.63E−15 | 5.27E−13 | yes |
| Ccr2 | NM_009915.2 | 1.873251084 | 2.41E−28 | 1.22E−25 | yes |
| H2-Ab1 | NM_207105.3 | 1.81029006 | 7.32E−20 | 2.23E−17 | yes |
| Itk | NM_010583.3 | 1.623223228 | 9.52E−06 | 0.000536295 | yes |
| Elane | NM_015779.2 | 1.584380476 | 1.92E−09 | 2.21E−07 | yes |
| Cd200r4 | NM_207244.2 | 1.519649166 | 2.66E−07 | 2.20E−05 | yes |
| Gbp4 | NM_001359082.1 | 1.369356142 | 0.000197453 | 0.007537622 | yes |
| Ciita | NM_001243761.2 | 1.351265777 | 7.22E−12 | 1.20E−09 | yes |
| Gm4951 | NM_001033767.3 | 1.339209413 | 2.12E−09 | 2.42E−07 | yes |
| Trem3 | NM_021407.3 | 1.334475621 | 3.98E−06 | 0.00025641 | yes |
| Ifi209 | NM_175026.3 | 1.244363836 | 2.16E−10 | 2.87E−08 | yes |
| Scimp | NM_001045526.2 | 1.237903217 | 0.000167009 | 0.006503806 | yes |
| Clec7a | NM_001309637.1 | 1.199563132 | 5.23E−06 | 0.000321085 | yes |
| Lpxn | NM_134152.3 | 1.173076287 | 8.88E−10 | 1.07E−07 | yes |
| Stat1 | NM_009283.4 | 1.141585617 | 4.22E−08 | 3.86E−06 | yes |
| Gm12185 | NM_001045540.2 | 1.126880183 | 1.44E−06 | 0.000105391 | yes |
| Ifit1bl1 | NM_001110517.1 | 1.083797998 | 3.73E−06 | 0.000241818 | yes |
| Zbp1 | NM_001139519.1 | 1.070373708 | 3.18E−07 | 2.62E−05 | yes |
| Rab44 | NM_001364848.1 | 1.065175904 | 1.75E−18 | 4.41E−16 | yes |
| Igtp | NM_018738.4 | 1.056428436 | 5.36E−05 | 0.002499037 | yes |
| Card9 | NM_001037747.1 | 1.027969368 | 2.47E−10 | 3.22E−08 | yes |
| Ffar2 | NM_001168511.1 | 1.023591181 | 0.000499193 | 0.016646943 | yes |
| Slfn2 | NM_011408.1 | 0.998297793 | 1.41E−06 | 0.000104741 | yes |
| Anxa3 | NM_013470.2 | 0.983477353 | 6.52E−06 | 0.000385931 | yes |
| Slamf8 | NM_029084.3 | 0.978304498 | 3.32E−07 | 2.71E−05 | yes |
| Mpo | NM_010824.2 | 0.96202403 | 0.000127902 | 0.005153844 | yes |
| Iigp1 | NM_021792.4 | 0.949899612 | 1.84E−09 | 2.13E−07 | yes |
| Irf8 | NM_008320.4 | 0.946506809 | 2.97E−06 | 0.000196816 | yes |
| Batf2 | NM_028967.1 | 0.941906969 | 1.94E−08 | 1.85E−06 | yes |
| Tyrobp | NM_011662.2 | 0.941672 | 8.46E−09 | 8.84E−07 | yes |
| Lilrb4a | NM_013532.3 | 0.924848828 | 0.000208423 | 0.007878671 | yes |
| Rab7b | NM_145509.3 | 0.919173496 | 8.12E−06 | 0.000461718 | yes |
| Mgl2 | NM_145137.2 | 0.885683947 | 0.000280262 | 0.009976799 | yes |
| Unc93b1 | NM_019449.2 | 0.869490089 | 0.000202935 | 0.007721496 | yes |
| Ctsg | NM_007800.2 | 0.854925088 | 0.000150209 | 0.005929157 | yes |
| Casp1 | NM_009807.2 | 0.846585949 | 4.69E−06 | 0.000291805 | yes |
| Ifit3 | NM_010501.2 | 0.836108093 | 4.07E−05 | 0.001947458 | yes |
| F830016B08Rik | NM_001101475.2 | 0.828760234 | 6.67E−07 | 5.16E−05 | yes |
| Il18r1 | NM_001161843.1 | 0.799828185 | 0.001055047 | 0.03115476 | yes |
| Gata1 | NM_008089.2 | 0.788765871 | 7.62E−05 | 0.003301222 | yes |
| Zbtb16 | NM_001364543.1 | 0.784981959 | 0.00099659 | 0.029654932 | yes |
| Pram1 | NM_001002842.2 | 0.771461883 | 0.000558731 | 0.018420648 | yes |
| Fcgr3 | NM_010188.5 | 0.765563142 | 2.68E−05 | 0.001352734 | yes |
| Prtn3 | NM_011178.2 | 0.762335806 | 0.000258436 | 0.009285285 | yes |
| Tnfsf8 | NM_009403.3 | 0.760523891 | 3.27E−05 | 0.001620475 | yes |
| Calr | NM_007591.3 | 0.72772945 | 0.001481617 | 0.040467492 | yes |
| Clnk | NM_013748.3 | 0.71063816 | 6.01E−05 | 0.002688244 | yes |
| Gbp2 | NM_010260.1 | 0.698188636 | 6.02E−05 | 0.002688244 | yes |
| Sell | NM_011346.2 | 0.677616606 | 0.000766436 | 0.024104293 | yes |
| Nlrc5 | NM_001033207.3 | 0.626051778 | 4.70E−06 | 0.000291805 | yes |
| Gbp5 | NM_153564.2 | 0.597709064 | 0.000774298 | 0.024285766 | yes |
| H2-Q5 | NR_051981.1 | 0.588961559 | 0.001129211 | 0.032881424 | yes |
| Fcgrt | NM_010189.3 | −0.633495972 | 0.001072863 | 0.031520447 | yes |
| Tinagl1 | NM_001168333.1 | −0.668087868 | 0.000140534 | 0.00556622 | yes |
| Axl | NM_009465.4 | −0.670820858 | 0.000316731 | 0.011206294 | yes |
| Tspan6 | NM_019656.3 | −0.778381184 | 4.21E−06 | 0.000268558 | yes |
| Rufy4 | NM_001170641.1 | −0.803313314 | 0.000896958 | 0.027537567 | yes |
| Pirb | NM_011095.2 | −0.842076828 | 1.32E−06 | 9.89E−05 | yes |
| Pld2 | NM_001361935.1 | −0.859615853 | 3.28E−06 | 0.000214819 | yes |
| Pdgfd | NM_027924.2 | −0.882330999 | 2.68E−05 | 0.001352734 | yes |
| Btla | NM_001037719.2 | −0.962662212 | 0.001152072 | 0.033258187 | yes |
| Ms4a2 | NM_013516.2 | −1.162752929 | 1.42E−06 | 0.000104789 | yes |
| AA467197 | NM_001004174.1 | −1.177116917 | 0.00103373 | 0.030603141 | yes |
| Fcrl1 | NM_178165.4 | −1.186661013 | 7.79E−06 | 0.000445481 | yes |
| Wfdc17 | NM_001081957.1 | −1.226358125 | 2.45E−05 | 0.001254412 | yes |
| Pdcd1 | NM_008798.2 | −1.241598958 | 7.60E−06 | 0.000436839 | yes |
| Icos | NM_017480.2 | −1.275435945 | 7.54E−06 | 0.000435503 | yes |
| Gcsam | NM_001159297.1 | −1.379466564 | 1.21E−15 | 2.56E−13 | yes |
| Ccl6 | NM_009139.3 | −1.414144764 | 9.57E−09 | 9.66E−07 | yes |
| Wfdc18 | NM_007969.4 | −1.605914897 | 3.06E−11 | 4.80E−09 | yes |

TABLE 1-continued

Genes modulated by Usp22-inhibition.

| Gene Name | Genbank Acc No. | log2 fold change | p-value | adjusted p-value | immune-related |
|---|---|---|---|---|---|
| Cd4 | NM_013488.2 | −1.607965397 | 6.34E−07 | 4.97E−05 | yes |
| C1qb | NM_009777.2 | −1.622380391 | 2.00E−06 | 0.000142223 | yes |
| Hcar2 | NM_030701.3 | −1.665447906 | 2.25E−06 | 0.000153569 | yes |
| Bank1 | NM_001033350.3 | −1.697470137 | 5.30E−08 | 4.77E−06 | yes |
| Fcer1a | NM_010184.2 | −1.771020515 | 4.55E−11 | 6.60E−09 | yes |
| Hmox1 | NM_010442.2 | −1.807938246 | 7.84E−11 | 1.11E−08 | yes |
| Treml4 | NM_172623.2 | −1.917891744 | 9.79E−06 | 0.000545995 | yes |
| Fcna | NM_007995.3 | −1.962884982 | 1.83E−10 | 2.47E−08 | yes |
| C1qc | NM_007574.2 | −2.000167294 | 4.01E−06 | 0.000257266 | yes |
| Cd200r3 | NM_001128132.1 | −2.069732901 | 1.06E−10 | 1.46E−08 | yes |
| Prg3 | NM_016914.2 | −2.187800268 | 8.71E−09 | 8.92E−07 | yes |
| Alox15 | NM_009660.3 | −2.566673763 | 8.67E−08 | 7.74E−06 | yes |
| Prg2 | NM_008920.4 | −2.606614737 | 0.000221364 | 0.008286881 | yes |
| Epx | NM_007946.2 | −4.204451238 | 1.26E−30 | 8.14E−28 | yes |
| Tmprss6 | NM_001355601.1 | 5.453577436 | 8.73E−12 | 1.43E−09 | no |
| Tmevpg1 | NR_104123.1 | 5.382518749 | 4.23E−07 | 3.44E−05 | no |
| Samd3 | NM_001115154.1 | 5.033153346 | 2.73E−38 | 3.16E−35 | no |
| Klra9 | NM_010651.3 | 5.012008568 | 9.91E−15 | 1.89E−12 | no |
| Klra3 | NM_001289605.1 | 5.00464563 | 1.84E−15 | 3.81E−13 | no |
| Gm4956 | NR_002858.1 | 4.90256644 | 3.03E−19 | 8.00E−17 | no |
| Klrc2 | NM_001098669.1 | 4.81152951 | 5.38E−25 | 2.50E−22 | no |
| Fasl | NM_010177.4 | 4.645334846 | 3.34E−24 | 1.49E−21 | no |
| Klrb1a | NM_010737.3 | 4.523433231 | 1.44E−19 | 4.06E−17 | no |
| Prss2 | NM_009430.2 | 4.348850799 | 6.69E−09 | 7.19E−07 | no |
| Klri2 | NM_177155.4 | 4.217292307 | 2.38E−28 | 1.22E−25 | no |
| Klra7 | NM_014194.5 | 4.078145415 | 4.02E−31 | 2.91E−28 | no |
| Klrc3 | NM_021378.1 | 3.830094942 | 3.67E−11 | 5.60E−09 | no |
| Cd7 | NM_009854.2 | 3.791406574 | 4.06E−22 | 1.57E−19 | no |
| Sh2d2a | NM_001025571.2 | 3.601290384 | 4.73E−16 | 1.04E−13 | no |
| Adgrg5 | NM_001145972.1 | 3.417630942 | 6.83E−32 | 5.28E−29 | no |
| Cxcr3 | NM_009910.3 | 3.145590325 | 4.08E−18 | 9.72E−16 | no |
| Ccr5 | NM_009917.5 | 3.077482789 | 3.05E−16 | 6.81E−14 | no |
| Ms4a4b | NM_021718.2 | 3.069293366 | 4.90E−38 | 5.17E−35 | no |
| Mirlet7d | NR_029656.1 | 2.811135252 | 0.000464464 | 0.015806767 | no |
| Gas7 | NM_008088.5 | 2.721907663 | 3.31E−23 | 1.37E−20 | no |
| Sytl3 | NM_031395.2 | 2.594332274 | 6.58E−13 | 1.19E−10 | no |
| Skap1 | NM_001177899.1 | 2.52182699 | 2.18E−10 | 2.87E−08 | no |
| Hsd11b1 | NM_008288.2 | 2.285221348 | 1.75E−12 | 3.04E−10 | no |
| Gimap4 | NM_174990.4 | 2.2594697 | 1.85E−19 | 5.11E−17 | no |
| Ms4a4c | NM_029499.3 | 2.209356231 | 1.01E−43 | 1.95E−40 | no |
| Itgax | NM_021334.2 | 2.191407814 | 2.27E−06 | 0.000154029 | no |
| Arl4d | NM_025404.3 | 2.144212922 | 2.61E−07 | 2.20E−05 | no |
| F13a1 | NM_028784.3 | 2.143113174 | 4.22E−32 | 3.50E−29 | no |
| Baiap3 | NM_001163270.1 | 1.990288458 | 1.48E−05 | 0.000803846 | no |
| Id2 | NM_010496.3 | 1.957322142 | 2.01E−20 | 6.85E−18 | no |
| Gimap3 | NM_031247.3 | 1.953065872 | 5.52E−07 | 4.39E−05 | no |
| Klrb1f | NM_153094.2 | 1.904853859 | 4.44E−19 | 1.14E−16 | no |
| Slc2a6 | NM_172659.2 | 1.896020939 | 3.02E−15 | 5.94E−13 | no |
| Gm12596 | NR_105031.1 | 1.805905975 | 5.24E−07 | 4.19E−05 | no |
| Ly6k | NM_029627.2 | 1.790387925 | 1.69E−08 | 1.65E−06 | no |
| Ly86 | NM_010745.2 | 1.750908886 | 2.04E−06 | 0.000144312 | no |
| Cldn13 | NM_020504.4 | 1.734358054 | 3.32E−12 | 5.58E−10 | no |
| Plbd1 | NM_025806.2 | 1.642699884 | 1.79E−09 | 2.10E−07 | no |
| Xdh | NM_011723.3 | 1.616603497 | 1.65E−05 | 0.000881881 | no |
| Igsf6 | NM_030691.1 | 1.615108455 | 1.43E−19 | 4.06E−17 | no |
| Clec5a | NM_021364.2 | 1.612207911 | 1.04E−08 | 1.05E−06 | no |
| Apol9b | NM_001168660.1 | 1.556789576 | 5.15E−07 | 4.15E−05 | no |
| Rhag | NM_011269.2 | 1.533710276 | 9.05E−08 | 8.02E−06 | no |
| Gdf3 | NM_008108.4 | 1.533433704 | 1.06E−06 | 8.02E−05 | no |
| Id3 | NM_008321.2 | 1.523382942 | 5.86E−06 | 0.000356217 | no |
| Majin | NM_001377075.1 | 1.516230596 | 8.58E−09 | 8.89E−07 | no |
| Cldn15 | NM_021719.4 | 1.48075101 | 5.28E−09 | 5.78E−07 | no |
| Tcf7 | NM_009331.4 | 1.475886056 | 2.84E−05 | 0.001414628 | no |
| Sema4a | NM_001163489.1 | 1.421447217 | 4.81E−05 | 0.002259292 | no |
| Serpina3f | NM_001168294.1 | 1.405559282 | 4.29E−06 | 0.000271948 | no |
| Gm15915 | NR_038017.1 | 1.37907016 | 2.11E−06 | 0.00014742 | no |
| Camk2b | NM_001174054.1 | 1.338459804 | 0.000176432 | 0.006824971 | no |
| Slc4a8 | NM_001347102.1 | 1.318114368 | 3.25E−09 | 3.63E−07 | no |
| Gbp3 | NM_001289493.1 | 1.314812205 | 4.11E−18 | 9.72E−16 | no |
| Cxcl10 | NM_021274.2 | 1.287976365 | 3.34E−05 | 0.00164062 | no |
| Ctsw | NM_009985.5 | 1.278383264 | 1.29E−06 | 9.75E−05 | no |
| Itga2b | NM_010575.2 | 1.27741917 | 0.000191468 | 0.007357571 | no |
| Epor | NM_010149.3 | 1.268358974 | 5.56E−05 | 0.002558676 | no |
| Tspo2 | NM_027292.2 | 1.267856338 | 1.10E−13 | 2.03E−11 | no |
| Lim2 | NM_177693.3 | 1.26484973 | 2.29E−05 | 0.001188368 | no |

TABLE 1-continued

| Genes modulated by Usp22-inhibition. | | | | | |
|---|---|---|---|---|---|
| Gene Name | Genbank Acc No. | log2 fold change | p-value | adjusted p-value | immune-related |
| Ly6c2 | NM_001099217.1 | 1.259253802 | 4.03E−05 | 0.001938891 | no |
| Tmod1 | NM_021883.2 | 1.242400794 | 0.000253578 | 0.009196175 | no |
| Ly6i | NM_001358005.1 | 1.225402295 | 5.67E−05 | 0.002602437 | no |
| Endog | NM_007931.1 | 1.191122932 | 0.000241694 | 0.008904311 | no |
| Traf1 | NM_001326601.1 | 1.175824878 | 0.000668409 | 0.021546917 | no |
| Nrp1 | NM_008737.2 | 1.170066283 | 1.64E−07 | 1.40E−05 | no |
| Mt1 | NM_013602.3 | 1.163802881 | 6.97E−09 | 7.42E−07 | no |
| Kcnip3 | NM_019789.4 | 1.156468998 | 4.22E−10 | 5.21E−08 | no |
| Gadd45g | NM_011817.2 | 1.152772157 | 1.94E−05 | 0.001021412 | no |
| Clca3a1 | NM_009899.4 | 1.148128829 | 3.01E−06 | 0.000198653 | no |
| Olfr632 | NM_147119.1 | 1.147114675 | 0.000916235 | 0.027981322 | no |
| Phf11d | NM_199015.4 | 1.143651718 | 4.48E−06 | 0.000280985 | no |
| Aoah | NM_012054.4 | 1.11248975 | 1.19E−07 | 1.03E−05 | no |
| F630028O10Rik | NR_030718.1 | 1.104838076 | 0.000403085 | 0.014005402 | no |
| Stxbp4 | NM_011505.2 | 1.086176232 | 1.06E−09 | 1.27E−07 | no |
| Mt2 | NM_008630.2 | 1.070877076 | 0.000430203 | 0.01481456 | no |
| Ehd3 | NM_020578.3 | 1.070628317 | 6.52E−05 | 0.002867717 | no |
| Id1 | NM_010495.3 | 1.04447986 | 9.28E−05 | 0.003903619 | no |
| Ms4a3 | NM_133246.5 | 1.023298123 | 0.000134929 | 0.00539284 | no |
| Gypa | NM_010369.3 | 1.017142892 | 5.05E−06 | 0.000311719 | no |
| Gimap7 | NM_146167.3 | 1.006600476 | 3.42E−06 | 0.000222712 | no |
| Hp | NM_017370.2 | 0.994349729 | 0.000184991 | 0.007132298 | no |
| Ces2g | NM_197999.2 | 0.972095825 | 0.000213046 | 0.008027288 | no |
| Socs2 | NM_007706.4 | 0.970212026 | 0.000220864 | 0.008286881 | no |
| Brat1 | NM_001276287.1 | 0.96878456 | 0.001752449 | 0.046657559 | no |
| Podnl1 | NM_001013384.2 | 0.960412721 | 0.000847747 | 0.026234941 | no |
| AW112010 | NR_102366.1 | 0.952964792 | 6.12E−09 | 6.64E−07 | no |
| Hvcn1 | NM_028752.3 | 0.940659896 | 2.19E−06 | 0.000151405 | no |
| Pmaip1 | NM_021451.2 | 0.926362407 | 0.000194711 | 0.007457498 | no |
| Ms4a6c | NM_001166376.1 | 0.904381039 | 0.00015523 | 0.006106598 | no |
| 1110008P14Rik | NM_198001.2 | 0.881981986 | 0.000243853 | 0.008927169 | no |
| A530032D15Rik | NM_213615.2 | 0.877096806 | 0.001755471 | 0.046657559 | no |
| Naaa | NM_025972.4 | 0.877012743 | 4.08E−05 | 0.001947458 | no |
| Tifab | NM_001168615.1 | 0.874953869 | 0.000671825 | 0.021597019 | no |
| Slc6a9 | NM_008135.4 | 0.873202819 | 0.000822249 | 0.025641753 | no |
| Slc12a4 | NM_009195.3 | 0.858902613 | 1.55E−05 | 0.000834124 | no |
| Mfsd2b | NM_001033488.2 | 0.798598454 | 0.001757666 | 0.046657559 | no |
| Cntd1 | NM_026562.2 | 0.797355032 | 9.47E−06 | 0.000536295 | no |
| Tacstd2 | NM_020047.3 | 0.79049102 | 2.36E−05 | 0.001217133 | no |
| Apol7e | NM_001134802.1 | 0.780194816 | 6.36E−06 | 0.000379835 | no |
| F2rl2 | NM_010170.4 | 0.780040347 | 2.43E−05 | 0.001247695 | no |
| Cpne5 | NM_153166.2 | 0.770746853 | 0.001176622 | 0.033798755 | no |
| Pmm1 | NM_013872.4 | 0.758560032 | 4.11E−05 | 0.001955555 | no |
| Gm12250 | NM_001135115.1 | 0.734516369 | 1.73E−10 | 2.36E−08 | no |
| Gria3 | NM_016886.4 | 0.725408721 | 6.38E−06 | 0.000379835 | no |
| Plac8 | NM_139198.2 | 0.700705492 | 0.001090664 | 0.031882018 | no |
| 5830428M24Rik | NR_038060.1 | 0.689031658 | 7.93E−05 | 0.003395644 | no |
| Apba3 | NM_018758.2 | 0.682636396 | 0.00113052 | 0.032881424 | no |
| Upp1 | NM_001159402.1 | 0.671412382 | 0.000396825 | 0.013829295 | no |
| Phldb2 | NM_153412.4 | 0.669395459 | 0.000478612 | 0.016099391 | no |
| Car1 | NM_009799.4 | 0.659973108 | 0.000270225 | 0.009649117 | no |
| I730030J21Rik | NR_045782.1 | 0.659015553 | 1.96E−05 | 0.001030695 | no |
| AB124611 | NM_001198794.1 | 0.649450998 | 0.000924996 | 0.028174753 | no |
| Ms4a6b | NM_027209.3 | 0.643120162 | 1.42E−05 | 0.000773937 | no |
| Bhlhe40 | NM_011498.4 | 0.641529183 | 0.001879706 | 0.049241521 | no |
| Fam189b | NM_001014995.1 | 0.635791229 | 0.001354521 | 0.037695951 | no |
| Icam4 | NM_023892.2 | 0.635767261 | 2.69E−05 | 0.001353527 | no |
| Nkg7 | NM_024253.4 | 0.626098893 | 7.48E−06 | 0.000434014 | no |
| 5830416I19Rik | NR_045384.1 | 0.618483881 | 0.001764217 | 0.046657559 | no |
| Dcun1d4 | NM_178896.5 | 0.613634686 | 0.001700031 | 0.045563177 | no |
| Itgb3 | NM_016780.2 | 0.613400103 | 0.000806989 | 0.025242868 | no |
| Usp18 | NM_011909.2 | 0.58755899 | 0.000339705 | 0.011982601 | no |
| Hemgn | NM_053149.2 | 0.585396311 | 0.00082416 | 0.025641753 | no |
| Phf14 | NM_001168382.1 | −0.58911535 | 7.49E−05 | 0.003259679 | no |
| Hoxa9 | NM_010456.3 | −0.590523235 | 0.001482006 | 0.040467492 | no |
| Slc24a5 | NM_175034.3 | −0.597791394 | 0.000396338 | 0.013829295 | no |
| Tst | NM_009437.4 | −0.599176815 | 2.10E−06 | 0.00014742 | no |
| Gm16973 | NR_046209.1 | −0.601662938 | 0.001218599 | 0.034832126 | no |
| Phlpp1 | NM_133821.3 | −0.603517344 | 0.00020388 | 0.007732106 | no |
| Ccdc149 | NM_001256059.1 | −0.610434576 | 0.000661941 | 0.021397855 | no |
| Rora | NM_001289916.1 | −0.610815594 | 0.000480148 | 0.016104394 | no |
| Phf13 | NM_172705.2 | −0.610912643 | 9.57E−05 | 0.003981508 | no |
| Cep85l | NM_001204983.1 | −0.611475346 | 0.000929414 | 0.028235202 | no |
| Pnck | NM_001199352.1 | −0.615943873 | 9.89E−05 | 0.004083379 | no |
| Otos | NM_153114.2 | −0.616161102 | 0.000862555 | 0.026622199 | no |

TABLE 1-continued

| Genes modulated by Usp22-inhibition. | | | | | |
|---|---|---|---|---|---|
| Gene Name | Genbank Acc No. | log2 fold change | p-value | adjusted p-value | immune-related |
| Tctn2 | NM_026486.3 | −0.620681528 | 0.00010642 | 0.004363955 | no |
| Marveld1 | NM_183195.2 | −0.621250055 | 8.73E−05 | 0.003697546 | no |
| Tubb4a | NM_009451.3 | −0.624610166 | 0.00025288 | 0.009196175 | no |
| Dmwd | NM_010058.2 | −0.628374483 | 0.001603163 | 0.043266749 | no |
| Sdc2 | NM_008304.2 | −0.62871418 | 0.000694566 | 0.022266416 | no |
| Gpsm2 | NM_029522.2 | −0.629491741 | 9.54E−05 | 0.003981508 | no |
| Msi2 | NM_001363195.1 | −0.63749623 | 0.000223407 | 0.008336454 | no |
| Cdk18 | NM_008795.2 | −0.640722864 | 8.64E−05 | 0.003674176 | no |
| Ptpn3 | NM_011207.2 | −0.641037926 | 0.000726696 | 0.023104958 | no |
| Hpgds | NM_019455.4 | −0.645772406 | 0.001436323 | 0.039498879 | no |
| Ptpdc1 | NM_001374755.1 | −0.655552125 | 0.00016312 | 0.00637375 | no |
| Sqrdl | NM_021507.5 | −0.66773788 | 5.76E−05 | 0.002626405 | no |
| Fstl1 | NM_008047.5 | −0.674911664 | 2.42E−07 | 2.05E−05 | no |
| Rhobtb3 | NM_028493.2 | −0.689550535 | 4.62E−05 | 0.002178634 | no |
| Rnf150 | NM_177378.4 | −0.699108787 | 0.000446349 | 0.015325083 | no |
| Lima1 | NM_001113545.1 | −0.702526352 | 1.11E−05 | 0.000614256 | no |
| Fhl1 | NM_010211.3 | −0.703333446 | 4.46E−05 | 0.002113498 | no |
| Pde8a | NM_008803.2 | −0.703610308 | 0.000900595 | 0.027576275 | no |
| Ak1 | NM_001198791.1 | −0.713972947 | 0.000255468 | 0.00923585 | no |
| Lonrf3 | NM_028894.1 | −0.714780127 | 1.05E−07 | 9.19E−06 | no |
| Ptk7 | NM_175168.4 | −0.715520764 | 1.63E−05 | 0.000877214 | no |
| Arhgef25 | NM_028027.3 | −0.719029129 | 0.000173033 | 0.006715895 | no |
| Fzd6 | NM_001162494.1 | −0.721574802 | 0.000100985 | 0.004155771 | no |
| Fsd2 | NM_172904.2 | −0.72666803 | 0.001201748 | 0.034435279 | no |
| Spic | NM_011461.3 | −0.743528179 | 6.21E−05 | 0.002750493 | no |
| Epha7 | NM_010141.4 | −0.747698679 | 0.00013262 | 0.005325431 | no |
| C77080 | NM_001285867.1 | −0.769431725 | 7.97E−05 | 0.003398771 | no |
| Basp1 | NM_027395.2 | −0.769527443 | 5.82E−05 | 0.002639943 | no |
| C030037D09Rik | NR_038058.1 | −0.774076843 | 0.000492779 | 0.016480406 | no |
| Efna4 | NM_007910.2 | −0.776332981 | 0.001587263 | 0.043037808 | no |
| Calml4 | NM_138304.2 | −0.779710627 | 0.001253524 | 0.035272217 | no |
| Serpinb8 | NM_011459.4 | −0.781216827 | 0.00122945 | 0.034858579 | no |
| Cd200 | NM_001358443.1 | −0.78517632 | 9.73E−06 | 0.000545534 | no |
| Myo5c | NM_001081322.1 | −0.785762837 | 6.63E−06 | 0.000388496 | no |
| Cdcp1 | NM_133974.3 | −0.786369491 | 0.000616687 | 0.020159586 | no |
| Nav1 | NM_173437.2 | −0.794263989 | 5.45E−05 | 0.002530836 | no |
| Akr1c12 | NM_013777.2 | −0.807939847 | 9.54E−05 | 0.003981508 | no |
| Fam196a | NM_001143802.1 | −0.814811346 | 5.55E−05 | 0.002558676 | no |
| Tpm2 | NM_001277876.1 | −0.831136108 | 1.35E−05 | 0.000737191 | no |
| Ltbp3 | NM_008520.2 | −0.831504366 | 0.001012601 | 0.030054302 | no |
| Angptl2 | NM_011923.4 | −0.835215151 | 5.91E−05 | 0.002669876 | no |
| Snn | NM_009223.3 | −0.838274923 | 0.00162832 | 0.043742244 | no |
| Cc2d2a | NM_001359906.1 | −0.840589494 | 5.98E−06 | 0.000359699 | no |
| Rnase4 | NM_021472.4 | −0.847958806 | 2.71E−05 | 0.001356624 | no |
| Fgd5 | NM_172731.3 | −0.856499769 | 5.81E−06 | 0.000354852 | no |
| Coro2b | NM_175484.3 | −0.858373181 | 1.19E−05 | 0.000656526 | no |
| Gab1 | NM_021356.2 | −0.858755667 | 2.22E−06 | 0.000152773 | no |
| Park2 | NM_016694.4 | −0.864764843 | 0.000162035 | 0.006352775 | no |
| Sgsm1 | NM_001309528.1 | −0.867117213 | 7.69E−05 | 0.003317016 | no |
| Serpinf1 | NM_011340.3 | −0.878189679 | 0.000474945 | 0.016022482 | no |
| Hoxa5 | NM_010453.5 | −0.881226682 | 0.0006435 | 0.020918252 | no |
| 4930509E16Rik | NR_045735.1 | −0.884885402 | 0.000944782 | 0.028478443 | no |
| Obsl1 | NM_001310679.1 | −0.891577916 | 2.55E−05 | 0.00129867 | no |
| Rassf6 | NM_028478.3 | −0.89800388 | 1.87E−06 | 0.000133845 | no |
| Eps8 | NM_001271595.1 | −0.899603169 | 3.91E−05 | 0.001898048 | no |
| Slc35d3 | NM_029529.3 | −0.905312813 | 5.77E−05 | 0.002626405 | no |
| Mfap2 | NM_001161799.1 | −0.906786291 | 9.67E−05 | 0.004009331 | no |
| Npr2 | NM_173788.3 | −0.907801555 | 0.000604155 | 0.019861798 | no |
| Hlf | NM_172563.3 | −0.908543057 | 1.34E−11 | 2.13E−09 | no |
| Ecscr | NM_001368651.1 | −0.910305406 | 7.50E−05 | 0.003259679 | no |
| Spag8 | NM_001290462.2 | −0.916941022 | 0.001142833 | 0.033074716 | no |
| Ppargc1a | NM_008904.2 | −0.918274417 | 1.40E−07 | 1.20E−05 | no |
| Kazald1 | NM_178929.4 | −0.919035185 | 5.98E−05 | 0.002688244 | no |
| Rbm47 | NM_001127382.2 | −0.933800561 | 1.89E−08 | 1.83E−06 | no |
| Rftn2 | NM_028713.1 | −0.933835302 | 1.02E−05 | 0.000564952 | no |
| Fxyd1 | NM_019503.4 | −0.936254337 | 0.000645698 | 0.020931076 | no |
| 9230110C19Rik | NM_199017.2 | −0.939766957 | 4.32E−06 | 0.000272634 | no |
| Mapk12 | NM_013871.3 | −0.943064445 | 6.58E−06 | 0.000387681 | no |
| Lrrn4 | NM_177303.4 | −0.943382731 | 2.40E−06 | 0.000162092 | no |
| Mylk | NM_139300.3 | −0.943481696 | 3.75E−09 | 4.14E−07 | no |
| Mpzl1 | NM_001083897.1 | −0.945660348 | 2.89E−06 | 0.000192754 | no |
| Inha | NM_010564.4 | −0.947109293 | 0.000115506 | 0.004703308 | no |
| Emcn | NM_001163522.1 | −0.948141243 | 1.39E−08 | 1.38E−06 | no |
| Cacna2d4 | NM_001362214.1 | −0.949115387 | 3.37E−05 | 0.00165012 | no |
| Scin | NM_001146196.1 | −0.951705161 | 0.00036927 | 0.012985994 | no |

TABLE 1-continued

Genes modulated by Usp22-inhibition.

| Gene Name | Genbank Acc No. | log2 fold change | p-value | adjusted p-value | immune-related |
|---|---|---|---|---|---|
| Zfp57 | NR_033137.1 | −0.961551526 | 3.13E−10 | 3.95E−08 | no |
| Sdc1 | NM_011519.2 | −0.970679418 | 8.76E−09 | 8.92E−07 | no |
| Pagr5 | NM_028748.2 | −0.975844113 | 3.67E−05 | 0.001787334 | no |
| Ccm2l | NM_001372363.1 | −0.98483084 | 0.000258129 | 0.009285285 | no |
| Pygm | NM_011224.2 | −0.991965671 | 5.94E−06 | 0.000359075 | no |
| Gas6 | NM_019521.2 | −0.993866349 | 2.76E−06 | 0.000185028 | no |
| Aldoc | NM_001303423.1 | −0.999672375 | 0.000611881 | 0.020058969 | no |
| Ankrd6 | NM_001012451.1 | −1.013011421 | 5.74E−07 | 4.53E−05 | no |
| Palld | NM_001293772.1 | −1.035940346 | 1.63E−06 | 0.000117937 | no |
| Tnfsf12 | NM_011614.3 | −1.036563482 | 6.85E−05 | 0.00299862 | no |
| Alpk3 | NM_054085.2 | −1.08079162 | 5.78E−11 | 8.28E−09 | no |
| Snx31 | NM_025712.4 | −1.082162683 | 4.18E−11 | 6.22E−09 | no |
| Adgre1 | NM_010130.4 | −1.093442008 | 1.81E−06 | 0.00013044 | no |
| Vldlr | NM_013703.2 | −1.111556553 | 2.82E−09 | 3.18E−07 | no |
| Afp | NM_007423.4 | −1.135961323 | 4.75E−08 | 4.30E−06 | no |
| 4930447C04Rik | NM_029444.2 | −1.145044436 | 1.67E−05 | 0.000888866 | no |
| Capsl | NM_029341.1 | −1.155057432 | 9.16E−11 | 1.28E−08 | no |
| Irf6 | NM_016851.2 | −1.157021277 | 6.43E−10 | 7.85E−08 | no |
| Prkcdbp | NM_028444.1 | −1.159445626 | 8.82E−07 | 6.78E−05 | no |
| Enkur | NM_027728.2 | −1.169499435 | 1.44E−06 | 0.000105391 | no |
| Slc40a1 | NM_016917.2 | −1.170090856 | 2.17E−06 | 0.000150865 | no |
| Fgf11 | NM_001362623.1 | −1.18720698 | 4.22E−10 | 5.21E−08 | no |
| Cpxm1 | NM_019696.2 | −1.201450234 | 3.48E−08 | 3.26E−06 | no |
| Marcks | NM_008538.2 | −1.204367822 | 0.000140378 | 0.00556622 | no |
| Rnase12 | NM_001011875.2 | −1.2050238 | 0.001075991 | 0.031532501 | no |
| Sema3d | NM_028882.4 | −1.215884434 | 0.001444734 | 0.039636265 | no |
| Kynu | NM_001289593.1 | −1.267542016 | 1.06E−07 | 9.21E−06 | no |
| Clec1a | NM_175526.3 | −1.388896943 | 2.21E−05 | 0.001152204 | no |
| Emp1 | NM_010128.4 | −1.5064867 | 1.95E−08 | 1.85E−06 | no |
| Krt7 | NM_033073.3 | −1.50817817 | 1.88E−05 | 0.000994214 | no |
| Mcpt8 | NM_008572.1 | −1.514203658 | 6.40E−07 | 4.98E−05 | no |
| Pde6h | NM_023898.4 | −1.52871342 | 2.11E−05 | 0.001104136 | no |
| Vcam1 | NM_011693.3 | −1.546848412 | 3.97E−08 | 3.65E−06 | no |
| Ddx4 | NM_010029.2 | −1.586679106 | 1.29E−29 | 7.48E−27 | no |
| Smoc1 | NM_022316.2 | −1.613398784 | 1.37E−12 | 2.41E−10 | no |
| C1qa | NM_007572.2 | −1.627288638 | 3.30E−05 | 0.001628772 | no |
| Mapk13 | NM_011950.2 | −1.714863562 | 2.63E−07 | 2.20E−05 | no |
| Itgb5 | NM_001145884.1 | −1.798206631 | 1.17E−09 | 1.38E−07 | no |
| Fabp4 | NM_024406.2 | −1.82320943 | 7.39E−09 | 7.79E−07 | no |
| Cyp11a1 | NM_019779.3 | −1.962699564 | 2.62E−10 | 3.37E−08 | no |
| Adgre4 | NM_139138.3 | −2.163981715 | 9.12E−07 | 6.96E−05 | no |
| Slc18a1 | NM_153054.2 | −2.198234058 | 3.71E−08 | 3.44E−06 | no |
| Efna1 | NM_010107.4 | −2.236784615 | 2.29E−16 | 5.21E−14 | no |
| Clec4a1 | NM_199311.2 | −2.380113738 | 1.06E−11 | 1.71E−09 | no |
| Usp22 | NM_001004143.4 | −2.394693671 | 2.68E−21 | 9.70E−19 | no |
| Clec4a3 | NM_153197.4 | −2.534742016 | 3.54E−11 | 5.48E−09 | no |
| Prss34 | NM_178372.2 | −2.627072019 | 1.27E−12 | 2.27E−10 | no |
| Hpgd | NM_008278.2 | −2.80838667 | 3.32E−20 | 1.10E−17 | no |
| Cd209f | NM_026956.2 | −8.001992737 | 4.38E−11 | 6.43E−09 | no |

Example 4: In Vivo Assay

As shown above, loss of Usp22 in hematopoietic cells results in enhanced HSC proliferation, myeloid bias and increased production of myeloid cells in the absence of infections. All of these phenotypes are typical hallmarks of "emergency hematopoiesis", normally occurring in response to infection. Therefore, the investigators next addressed the question whether Usp22 deficiency increases protection of mice against bacterial infections by "pre-activating" the immune system. To this end, Usp22 KO mice and their wildtype counterparts were intravenously infected with $10^4$ CFU *Listeria monocytogenes* (EGDe stain), and bacterial burden in different tissues of infected mice was assessed three days post infection. Within all of analyzed organs (blood, brain, liver and spleen), bacterial loads were markedly reduced in Usp22 KO compared to wildtype mice (FIG. 5A-D), strongly supporting protective rules of Usp22 deficiency in a bacterial infection. Since differences were apparent three days after infection, the immune-enhancing effects against bacterial infection caused by loss of Usp22 are most likely mediated through innate immune cells.

Example 5: Screening Method

Given the immune-enhancing effects of genetic Usp22 deficiency, a key goal is the identification of further small molecule inhibitors of USP22 for in vivo testing and use. In order to screen for substances capable of inhibiting USP22 using high throughput methods, the inventors developed an in vitro deubiquitination assay to measure the enzymatic activity of USP22. To this end, recombinant USP22 has been generated. The fluorogenic ubiquitin conjugate AMC-Ubiquitin, which becomes fluorescent upon deubiquitination of AMC, was used as a substrate for recombinant USP22 under different reaction conditions. As shown in FIG. 6, fluorescence resulting from the liberation of AMC increased over time in a USP22-dependent manner, demonstrating the feasibility of a high throughput screening assay to identify small molecule inhibitors of USP22. A comparative, affinity-based method for screening for USP22 inhibitors was published recently by Morgan et al. (2021), Cell Chem Biol 29:1-11 (doi.org/10.1016/j.chembiol.2021.12.004).

LITERATURE

Ivashkiv et al, Nature Rev Immunol 14, 36-49(2014)
Jeusset & MacManus, Cancers 9:167 (2017)
Karlowitz et al. (2022), bioRxiv preprint doi.org/10.1101/2022.02.01.478628
Morgan et al. (2021), Cell Chem Biol 29:1-11 (doi.org/10.1016/j.chembiol.2021.12.004)
Roedig et al. (2020), EMBO reports 22:e50163
Schneider et al., Annu. Rev. Immunol. 32, 513-545 (2014)
Wang et al., Cancer Res 75(15) Supplement:Abstract 5432
Zhang et al, Molecular Cell 29, 102-111 (2008)

The invention claimed is:

1. A method for activating an immune response in a subject in need thereof, the method comprising administering an inhibitor of ubiquitin-specific peptidase 22 (Usp22 inhibitor) to said subject, wherein the activation of an immune response is treatment of a virus infection, of a bacterial infection, of a fungal infection, or of an autoimmune disease.

2. The method of claim 1, wherein the activation of an immune response is activation of an interferon-response, is an activation of phagocytes, dendritic cells, and/or granulocytes; and/or causes a myeloid bias.

3. The method of claim 1, wherein said virus infection is hepatitis B or C infection and/or wherein said autoimmune disease is multiple sclerosis.

4. The method of claim 1, wherein said Usp22 inhibitor is a direct Usp22 inhibitor, preferably is a polypeptide, polynucleotide, or small molecule, specifically binding and inhibiting Usp22.

5. The method of claim 1, wherein said Usp22 inhibitor is selected from the list consisting of an antibody, an aptamer, an anticalin, and a Designed Ankyrin Repeat Protein (DARPin).

6. The method of claim 1, wherein said Usp22 inhibitor is an indirect Usp22 inhibitor, preferably is a polynucleotide.

7. The method of claim 1, wherein said Usp22 inhibitor is selected from the list consisting of a shRNA, a siRNA, a miRNA agent, an antisense molecule, an antisense oligonucleotide, a ribozyme, and a pair of CRISPR/Cas oligonucleotides.

8. A method for identifying a subject susceptible to treatment of disease by administration of a Usp22 inhibitor comprising a) determining in a sample of said subject the amount of a Usp22 gene product, of monoubiquitinated H2B (H2Bub1) and/or of an interferon-stimulated gene, b) comparing said amount determined in step a) to a reference, and c) based on the result of step b), identifying a subject susceptible to treatment of disease by administration of a Usp22 inhibitor, wherein said disease is a virus infection, a bacterial infection, or an autoimmune disease.

9. A method for identifying a compound for activation of an immune response in a subject, comprising a) contacting a reaction mixture comprising a Ubiquitin-specific peptidase 22 and Histone 2B-ubiquitin conjugate (H2Bub1) with a compound suspected to have the activity of being an activator of said immune response, b) determining the deubiquitination of H2Bub1 in the reaction mixture, and c) identifying a compound for activation of an immune response based on the result of the determination step of b).

10. A method for identifying a compound for activation of an immune response in a subject, comprising (A) contacting a host cell with a compound suspected of being an activator of said immune response;

(B) determining the amount of H2Bub1 and/or of at least one H2Bub1 modulated gene of Table 1 in said host cell;

(C) comparing the amount or amounts determined in step (B) to a reference or to references; and (D) identifying a compound for activation of an immune response in a subject based on the result of comparison step (C).

* * * * *

SEQUENCE LISTING

```
<160> NUMBER OF SEQ ID NOS: 16

<210> SEQ ID NO 1
<211> LENGTH: 13
<212> TYPE: PRT
<213> ORGANISM: Artificial Sequence
<220> FEATURE:
<223> OTHER INFORMATION: hD1 linear inhibitory peptide
<220> FEATURE:
<221> NAME/KEY: MISC_FEATURE
<222> LOCATION: (1)..(1)
<223> OTHER INFORMATION: preferably is a D amino acid

<400> SEQUENCE: 1

Tyr Ala Ile Ser Tyr Arg Gly Lys Thr Thr Leu Leu Cys
1               5                   10


<210> SEQ ID NO 2
<211> LENGTH: 17
<212> TYPE: PRT
<213> ORGANISM: Artificial Sequence
<220> FEATURE:
<223> OTHER INFORMATION: hL1 linear inhibitory peptide

<400> SEQUENCE: 2

Tyr Thr Leu Asn Phe Arg Phe Trp Ser Asp His Ile Ser Trp Tyr Ser
1               5                   10                  15

Cys


<210> SEQ ID NO 3
<211> LENGTH: 14
<212> TYPE: PRT
<213> ORGANISM: Artificial Sequence
<220> FEATURE:
<223> OTHER INFORMATION: hD2 linear inhibitory peptide
<220> FEATURE:
<221> NAME/KEY: MISC_FEATURE
<222> LOCATION: (1)..(1)
<223> OTHER INFORMATION: preferably is a D amino acid

<400> SEQUENCE: 3

Tyr His Gln Trp Ser Tyr Arg Gly Ala Thr Tyr Arg Ser Cys
1               5                   10


<210> SEQ ID NO 4
<211> LENGTH: 16
<212> TYPE: PRT
<213> ORGANISM: Artificial Sequence
<220> FEATURE:
<223> OTHER INFORMATION: hD3 linear  inhibitory peptide
<220> FEATURE:
<221> NAME/KEY: MISC_FEATURE
<222> LOCATION: (1)..(1)
<223> OTHER INFORMATION: preferably is a D amino acid

<400> SEQUENCE: 4

Tyr Asn Gly Pro Ser Tyr Tyr Arg Leu Arg Ser Trp Leu Ser Ser Cys
1               5                   10                  15
```

<210> SEQ ID NO 5
<211> LENGTH: 15
<212> TYPE: PRT
<213> ORGANISM: Artificial Sequence
<220> FEATURE:
<223> OTHER INFORMATION: hD4 linear inhibitory peptide
<220> FEATURE:
<221> NAME/KEY: MISC_FEATURE
<222> LOCATION: (1)..(1)
<223> OTHER INFORMATION: preferably is a D amino acid

<400> SEQUENCE: 5

Tyr Trp Ile Thr His Ser Tyr Arg Gly Leu Ser Lys Ser Phe Cys
1 5 10 15

<210> SEQ ID NO 6
<211> LENGTH: 14
<212> TYPE: PRT
<213> ORGANISM: Artificial Sequence
<220> FEATURE:
<223> OTHER INFORMATION: hD5 linear inhibitory peptide
<220> FEATURE:
<221> NAME/KEY: MISC_FEATURE
<222> LOCATION: (1)..(1)
<223> OTHER INFORMATION: preferably is a D amino acid

<400> SEQUENCE: 6

Tyr Gln Thr Trp Ser Trp Arg Gly Arg Arg Tyr Ser Phe Cys
1 5 10

<210> SEQ ID NO 7
<211> LENGTH: 17
<212> TYPE: PRT
<213> ORGANISM: Artificial Sequence
<220> FEATURE:
<223> OTHER INFORMATION: yL1 linear inhibitory peptide

<400> SEQUENCE: 7

Tyr Leu His Asp Ser Ala Phe Ser Phe Gly Trp Ser Leu Arg Leu Tyr
1 5 10 15

Cys

<210> SEQ ID NO 8
<211> LENGTH: 14
<212> TYPE: PRT
<213> ORGANISM: Artificial Sequence
<220> FEATURE:
<223> OTHER INFORMATION: yD1 linear inhibitory peptide
<220> FEATURE:
<221> NAME/KEY: MISC_FEATURE
<222> LOCATION: (1)..(1)
<223> OTHER INFORMATION: preferably is a D amino acid

<400> SEQUENCE: 8

Tyr Arg Gln Trp Ser Phe Arg Gly Arg Thr Phe Trp Ser Cys
1 5 10

<210> SEQ ID NO 9
<211> LENGTH: 13
<212> TYPE: PRT
<213> ORGANISM: Artificial Sequence
<220> FEATURE:
<223> OTHER INFORMATION: hD1 cyclic inhibitory peptide
<220> FEATURE:
<221> NAME/KEY: MISC_FEATURE
<222> LOCATION: (1)..(1)
<223> OTHER INFORMATION: preferably is a D amino acid
<220> FEATURE:

-continued

```
<221> NAME/KEY: THIOETH
<222> LOCATION: (13)..(13)
<223> OTHER INFORMATION: Thioether formed with N-chloroacetyl-amino acid
      in pos. 1

<400> SEQUENCE: 9

Tyr Ala Ile Ser Tyr Arg Gly Lys Thr Thr Leu Leu Cys
1               5                   10


<210> SEQ ID NO 10
<211> LENGTH: 17
<212> TYPE: PRT
<213> ORGANISM: Artificial Sequence
<220> FEATURE:
<223> OTHER INFORMATION: hL1 cyclic inhibitory peptide
<220> FEATURE:
<221> NAME/KEY: THIOETH
<222> LOCATION: (17)..(17)
<223> OTHER INFORMATION: Thioether formed with N-chloroacetyl-amino acid
      in pos. 1

<400> SEQUENCE: 10

Tyr Thr Leu Asn Phe Arg Phe Trp Ser Asp His Ile Ser Trp Tyr Ser
1               5                   10                  15

Cys


<210> SEQ ID NO 11
<211> LENGTH: 14
<212> TYPE: PRT
<213> ORGANISM: Artificial Sequence
<220> FEATURE:
<223> OTHER INFORMATION: hD2 cyclic inhibitory peptide
<220> FEATURE:
<221> NAME/KEY: MISC_FEATURE
<222> LOCATION: (1)..(1)
<223> OTHER INFORMATION: preferably is a D amino acid
<220> FEATURE:
<221> NAME/KEY: THIOETH
<222> LOCATION: (14)..(14)
<223> OTHER INFORMATION: Thioether formed with N-chloroacetyl-amino acid
      in pos. 1

<400> SEQUENCE: 11

Tyr His Gln Trp Ser Tyr Arg Gly Ala Thr Tyr Arg Ser Cys
1               5                   10


<210> SEQ ID NO 12
<211> LENGTH: 16
<212> TYPE: PRT
<213> ORGANISM: Artificial Sequence
<220> FEATURE:
<223> OTHER INFORMATION: hD3 cyclic inhibitory peptide
<220> FEATURE:
<221> NAME/KEY: MISC_FEATURE
<222> LOCATION: (1)..(1)
<223> OTHER INFORMATION: preferably is a D amino acid
<220> FEATURE:
<221> NAME/KEY: THIOETH
<222> LOCATION: (16)..(16)
<223> OTHER INFORMATION: Thioether formed with N-chloroacetyl-amino acid
      in pos. 1

<400> SEQUENCE: 12

Tyr Asn Gly Pro Ser Tyr Tyr Arg Leu Arg Ser Trp Leu Ser Ser Cys
1               5                   10                  15


<210> SEQ ID NO 13
<211> LENGTH: 15
<212> TYPE: PRT
<213> ORGANISM: Artificial Sequence
```

<220> FEATURE:
<223> OTHER INFORMATION: hD4 inhibitory peptide
<220> FEATURE:
<221> NAME/KEY: MISC_FEATURE
<222> LOCATION: (1)..(1)
<223> OTHER INFORMATION: preferably is a D amino acid
<220> FEATURE:
<221> NAME/KEY: THIOETH
<222> LOCATION: (15)..(15)
<223> OTHER INFORMATION: Thioether formed with N-chloroacetyl-amino acid
in pos. 1

<400> SEQUENCE: 13

Tyr Trp Ile Thr His Ser Tyr Arg Gly Leu Ser Lys Ser Phe Cys
1 5 10 15

<210> SEQ ID NO 14
<211> LENGTH: 14
<212> TYPE: PRT
<213> ORGANISM: Artificial Sequence
<220> FEATURE:
<223> OTHER INFORMATION: hD5 inhibitory peptide
<220> FEATURE:
<221> NAME/KEY: MISC_FEATURE
<222> LOCATION: (1)..(1)
<223> OTHER INFORMATION: preferably is a D amino acid
<220> FEATURE:
<221> NAME/KEY: THIOETH
<222> LOCATION: (14)..(14)
<223> OTHER INFORMATION: Thioether formed with N-chloroacetyl-amino acid
in pos. 1

<400> SEQUENCE: 14

Tyr Gln Thr Trp Ser Trp Arg Gly Arg Arg Tyr Ser Phe Cys
1 5 10

<210> SEQ ID NO 15
<211> LENGTH: 17
<212> TYPE: PRT
<213> ORGANISM: Artificial Sequence
<220> FEATURE:
<223> OTHER INFORMATION: yL1 icyclic nhibitory peptide
<220> FEATURE:
<221> NAME/KEY: THIOETH
<222> LOCATION: (17)..(17)
<223> OTHER INFORMATION: Thioether formed with N-chloroacetyl-amino acid
in pos. 1

<400> SEQUENCE: 15

Tyr Leu His Asp Ser Ala Phe Ser Phe Gly Trp Ser Leu Arg Leu Tyr
1 5 10 15

Cys

<210> SEQ ID NO 16
<211> LENGTH: 14
<212> TYPE: PRT
<213> ORGANISM: Artificial Sequence
<220> FEATURE:
<223> OTHER INFORMATION: yD1 cyclic inhibitory peptide
<220> FEATURE:
<221> NAME/KEY: MISC_FEATURE
<222> LOCATION: (1)..(1)
<223> OTHER INFORMATION: preferably is a D amino acid
<220> FEATURE:

-continued

```
<221> NAME/KEY: THIOETH
<222> LOCATION: (14)..(14)
<223> OTHER INFORMATION: Thioether formed with N-chloroacetyl-amino acid
      in pos. 1

<400> SEQUENCE: 16

Tyr Arg Gln Trp Ser Phe Arg Gly Arg Thr Phe Trp Ser Cys
1               5                   10
```